(12) United States Patent
Nunnari et al.

(10) Patent No.: US 8,450,333 B2
(45) Date of Patent: May 28, 2013

(54) MOLECULES FOR REGULATING CELL DEATH

(75) Inventors: Jodi Nunnari, Davis, CA (US); Ann Cassidy-Stone, Davis, CA (US); Mark Kurth, Davis, CA (US)

(73) Assignee: The Regents of The University of California, Oakland, CA (US)

( * ) Notice: Subject to any disclaimer, the term of this patent is extended or adjusted under 35 U.S.C. 154(b) by 1360 days.

(21) Appl. No.: 12/028,536

(22) Filed: Feb. 8, 2008

(65) Prior Publication Data

US 2008/0287473 A1 Nov. 20, 2008

Related U.S. Application Data

(62) Division of application No. 10/865,542, filed on Jun. 9, 2004, now abandoned.

(60) Provisional application No. 60/542,347, filed on Feb. 4, 2004, provisional application No. 60/477,234, filed on Jun. 9, 2003.

(51) Int. Cl.
*A01N 43/54* (2006.01)
*A61K 31/517* (2006.01)
*C07D 239/72* (2006.01)

(52) U.S. Cl.
USPC ...................................... 514/266.31; 544/285

(58) Field of Classification Search
USPC ...................................... 514/266.31; 544/285
See application file for complete search history.

(56) References Cited

U.S. PATENT DOCUMENTS

| 4,861,780 A | 8/1989 | Takahashi et al. |
| 5,037,829 A | 8/1991 | Freyne et al. |
| 5,298,249 A | 3/1994 | Hani et al. |
| 2003/0220227 A1 | 11/2003 | Gungor et al. |

OTHER PUBLICATIONS

Bossy-Wetzel, E. et. al., "Mitochondrial fission in apoptosis, neurodegeneration and aging", Current Opinion in Cell Biology, vol. 15, 2003, pp. 706-716.*
Haviv, F. et al., "2-[(Phenylthio)methyl]pyridine Derivatives: New Antiinflammatory Agents", *Journal of Medicinal Chemistry*, 1983 26(2):218-222.
Hill, T. et al., "Small Molecule Inhibitors of Dynamin I GTPase Activity: Development of Dimeric Tyrphostins", *Journal of Medicinal Chemistry*, 2005 48:7781-7788.
Macia, E. et al., "Dynasore, a Cell-Permeable Inhibitor of Dynamin", *Developmental Cell 10*, 2006 10:839-850.

* cited by examiner

*Primary Examiner* — Paul V. Ward
(74) *Attorney, Agent, or Firm* — Morgan, Lewis & Bockius LLP; Jeffry S. Mann; Ada O. Wong

(57) ABSTRACT

The present invention provides compounds capable of regulating apoptosis, e.g., via regulating mitochondrial fission or fusion. The present invention also provides methods of screening for compounds capable of regulating apoptosis and methods of treating conditions association with apoptosis.

12 Claims, 16 Drawing Sheets

Compound A1

Compound C

Compound B

Compound A1

Compound A3

Compound A2

# MOLECULES FOR REGULATING CELL DEATH

CROSS-REFERENCE TO RELATED APPLICATIONS

This application is a divisional of U.S. Ser. No. 10/865,542 filed Jun. 9, 2004 which claims priority under 35 U.S.C. §119(e) from provisional application Nos. 60/477,234, filed Jun. 9, 2003; and 60/542,347 filed Feb. 4, 2004 all of which are hereby expressly incorporated by reference in their entireties.

This invention was made in part with government support under Grant No. NIH/GM 62942 awarded by the National Institutes of Health (NIH). The government may have certain rights in this invention.

FIELD OF THE INVENTION

This invention relates generally to the field of regulating cell death, especially apoptosis.

BACKGROUND OF THE INVENTION

In *S. cerevisiae*, mitochondria form a continuous reticulum evenly distributed at the cell cortex. The maintenance of this structure is a complex process dependent on cytoskeletal elements and mitochondrial-associated proteins. It has been shown by time-lapse analysis of mitochondrial dynamics that the continuity of this structure is also maintained by a balanced frequency of fission and fusion events. Mitochondrial fission has been observed to occur during apoptosis and has been shown to be required for this process.

There is a need in the art to provide methods and compositions useful for regulating cell death, especially apoptosis via regulating fission and fusion events of mitochondria.

SUMMARY OF THE INVENTION

The present invention is based, in part, on the discovery that cell death, e.g., apoptosis can be regulated via regulating mitochondrial dynamics, e.g., fission and fusion events of mitochondria.

In one embodiment, the present invention provides a compound having a formula as shown in FIG. 1 or its derivatives.

In another embodiment, a compound of the general formula is envisaged:

where $R_1$ may include, but is not limited to, H; a C1-C18 alkyl, which may be branched, may contain a heteroatom or may be substituted, or combinations thereof; a C1-C18 alkenyl, which may be branched, may contain a heteroatom or may be substituted, or combinations thereof; a C1-C18 alkynl, which may be branched, may contain a heteroatom or may be substituted, or combinations thereof; a C3-C18 aryl which may contain a side group, may contain a bridge, may contain a heteroatom or may be substituted, or combinations thereof; or a C5-C18 cycloalkyl which may contain a side group, may contain a bridge, may contain a heteroatom or may be substituted, or combinations thereof;

$R_2$ is H; a C1-C18 alkyl, which may be branched, may contain a heteroatom or may be substituted, or combinations thereof; or a halogen;

$R_3$ is H; a C1-C18 alkyl, which may be branched, may contain a heteroatom or may be substituted, or combinations thereof;

$R_4$ is H or a halogen; and $R_5$ is H or a halogen, with the provisos that when $R_3$ is H and $R_4$ is H or a halogen, $R_5$ is a halogen, or when $R_2$ is a halogen $R_5$ is H or a halogen, further the envisaged compound causes the formation of net like structures in mitochondria, inhibits mitochondrial fission, or inhibits apoptosis.

In a related aspect, such a compound may include, but is not limited to, 3-(2-fluorophenyl)-2-mercaptoquinolin-4 (3H)-one, 3-(2-chlorophenyl)-2-mercaptoquinolin-4(3H)-one, 3-(2-bromophenyl)-2-mercaptoquinolin-4(3H)-one, 3-(2,6-dichlorophenyl)-2-mercaptoquinolin-4(3H)-one, 3-(6-chlorophenyl)-2-mercaptoquinazolin-4(3H)-one, 3-(2, 4-dichlorophenyl)-2-mercaptoquinolin-4(3H)-one, 3-(2,4-dichloro-5-methoxyphenyl)-2-mercaptoquinazolin-4(3H)-one, 2-mercapto-3-O-tolyl-4(3H)-quinazolinone, 2-mercapto-3-(2-(trifluoromethyl)phenyl)quinazolin-4(3H)-one, and 2-mercapto-3-(2-ethyl-phenyl) quinazolin-4(3H)-one.

In one embodiment, a compound of the general formula is envisaged:

where M is C and n is an integer of 0 or 1;

wherein $R_1$ includes, but is not limited to, H; a C1-C18 alkyl, which may be branched, 7may contain a heteroatom or may be substituted, or combinations thereof; a C1-C18 alkenyl, which may be branched, may contain a heteroatom or may be substituted, or combinations thereof; a C1-C18 alkynl, which may be branched, may contain a heteroatom or may be substituted, or combinations thereof; a C3-C18 aryl which may contain a side group, may contain a bridge, may contain a heteroatom or may be substituted, or combinations thereof; or a C5-C18 cycloalkyl which may contain a side group, may contain a bridge, may contain a heteroatom or may be substituted, or combinations thereof;

$R_2$ is H; a C1-C18 alkyl, which may be branched, may contain a heteroatom or may be substituted, or combinations thereof; or a halogen;

$R_3$ is H; a C1-C18 alkyl, which may be branched, may contain a heteroatom or may be substituted, or combinations thereof;

$R_4$ is H or a halogen; and $R_5$ is H or a halogen, with the provisos that when $R_3$ is H and $R_4$ is H or a halogen, $R_5$ is a halogen, or when $R_2$ is a halogen $R_5$ is H or a halogen, further the envisaged compound causes the formation of net like structures in mitochondria, inhibit mitochondrial fission, or inhibiting apoptosis.

In another embodiment, a compound of the general formula is envisaged:

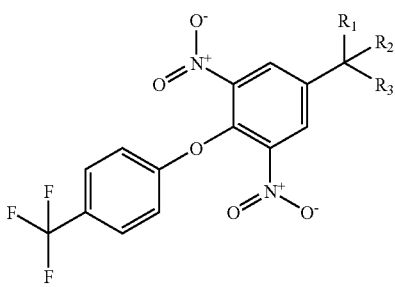

where $R_1$, $R_2$ and $R_3$ include, but are not limited to, H; a C1-C18 alkyl, which may be branched, may contain a heteroatom or may be substituted, or combinations thereof; a C1-C18 alkenyl, which may be branched, may contain a heteroatom or may be substituted, or combinations thereof; a C1-C18 alkynl, which may be branched, may contain a heteroatom or may be substituted, or combinations thereof; a C3-C18 aryl which may contain a side group, may contain a bridge, may contain a heteroatom or may be substituted, or combinations thereof; or a C5-C18 cycloalkyl which may contain a side group, may contain a bridge, may contain a heteroatom or may be substituted, or combinations thereof; or a halogen or a combination thereof, further the envisaged compound inhibits mitochondrial fusion or increases apoptosis.

In a related aspect, such a compound may include, but is not limited to, 1,3-dinitro-5-(trifluoromethyl)-2-(4-(trifluoromethyl)phenyoxy)benzene and 5-tert-butyl-1,3-dinitro-2-(4-(trifluoromethyl)phenoxy)benzene.

In one embodiment, a compound of the general formula is envisaged:

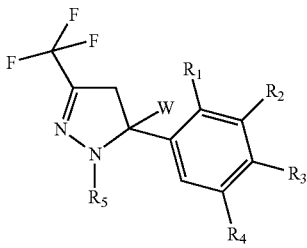

where W is H or O;

$R_1$ and $R_2$ include, but are not limited to, H; a C1-C18 alkyl, which may be branched, may contain a heteroatom or may be substituted, or combinations thereof; a C1-C18 alkenyl, which may be branched, may contain a heteroatom or may be substituted, or combinations thereof; a C1-C18 alkynl, which may be branched, may contain a heteroatom or may be substituted, or combinations thereof; a C3-C18 aryl which may contain a side group, may contain a bridge, may contain a heteroatom or may be substituted, or combinations thereof; or a C5-C18 cycloalkyl which may contain a side group, may contain a bridge, may contain a heteroatom or may be substituted, or combinations thereof; or may be combined to form a C5-18 cycloalkyl;

$R_3$ is a H or a C1-C18 alkyl, which may be branched, may contain a heteroatom or may be substituted, or combinations thereof;

$R_4$ is a H or a C1-C18 alkyl, which may be branched, may contain a heteroatom or may be substituted, or combinations thereof;

$R_5$ is H; a C1-C18 alkyl, which may be branched, may contain a heteroatom or may be substituted, or combinations thereof; a C1-C18 alkenyl, which may be branched, may contain a heteroatom or may be substituted, or combinations thereof; a C1-C18 alkynl, which may be branched, may contain a heteroatom or may be substituted, or combinations thereof; a C3-C18 aryl which may contain a side group, may contain a bridge, may contain a heteroatom or may be substituted, or combinations thereof; or a C5-C18 cycloalkyl which may contain a side group, may contain a bridge, may contain a heteroatom or may be substituted, or combinations thereof; or may be combined to form a C5-C18 cycloalkyl;

further the envisaged compound inhibits mitochondrial fusion or increases apoptosis.

In a related aspect, such a compound may include, but is not limited to, 5-(6-tert-butyl-1,1-dimethyl-2,3-dihydro-1H-inden-4-yl)-3-(trifluoromethyl)-4,5-dihydro-1H-pyrazole and 5-(6-bromobenzoyl)-5-(4-ethylphenyl)-3-(trifluoromethyl)-4,5-dihydro-1H-pyrazol-5-olate.

In another embodiment, a compound of the general formula is envisaged:

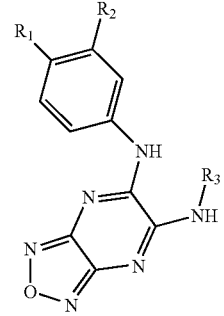

$R_1$ and $R_2$ include, but are not limited to, H; a C1-C18 alkyl, which may be branched, may contain a heteroatom or may be substituted, or combinations thereof; a C1-C18 alkenyl, which may be branched, may contain a heteroatom or may be substituted, or combinations thereof; a C1-C18 alkynl, which may be branched, may contain a heteroatom or may be substituted, or combinations thereof; a C3-C18 aryl which may contain a side group, may contain a bridge, may contain a heteroatom or may be substituted, or combinations thereof; or a C5-C18 cycloalkyl which may contain a side group, may contain a bridge, may contain a heteroatom or may be substituted, or a halogen; or combinations thereof;

R3 is are independently H; a C1-C18 alkyl, which may be branched, may contain a heteroatom or may be substituted, or combinations thereof; a C1-C18 alkenyl, which may be branched, may contain a heteroatom or may be substituted, or combinations thereof; a C1-C18 alkynl, which may be branched, may contain a heteroatom or may be substituted, or combinations thereof; a C3-C18 aryl which may contain a side group, may contain a bridge, may contain a heteroatom or may be substituted, or combinations thereof; or a C5-C18 cycloalkyl which may contain a side group, may contain a bridge, may contain a heteroatom or may be substituted, or a combination thereof, further the envisaged compound inhibits mitochondrial fusion or increases apoptosis.

In a related aspect, such a compound may include, but is not limited to, $N^5$-(4-chlorophenyl)-$N^6$-phenethyl-[1,2,5]oxadiazolo[3,4-b]pyrazine-5,6-diamine and $N^5$-cyclohexyl-$N^6$-6-(3,4-dimethylohenyl)-[1,2,5]oxadiazolo[3,4-b]pyrazine-5,6-diamine.

In one embodiment, a compound of the general formula is envisaged:

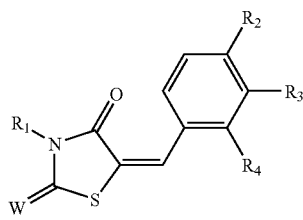

where
W is N or S;
$R_1$ is H or a C1-C3 alkyl or a substituted piperidine;
$R_2$ is H or a C1-C18 alkyl, which may be branched, may contain a heteroatom or may be substituted, or combinations thereof; a C1-C18 alkenyl, which may be branched, may contain a heteroatom or may be substituted, or combinations thereof; a C1-C18 alkynl, which may be branched, may contain a heteroatom or may be substituted, or combinations thereof; a C3-C18 aryl which may contain a side group, may contain a bridge, may contain a heteroatom or may be substituted, or combinations thereof; or a C5-C18 cycloalkyl which may contain a side group, may contain a bridge, may contain a heteroatom or may be substituted, or a combination thereof;
$R_3$ is H; O or a C1-C18 alkyl, which may be branched, may contain a heteroatom or may be substituted, or combinations thereof; a C1-C18 alkenyl, which may be branched, may contain a heteroatom or may be substituted, or combinations thereof; a C1-C18 alkynl, which may be branched, may contain a heteroatom or may be substituted, or combinations thereof; a C3-C18 aryl which may contain a side group, may contain a bridge, may contain a heteroatom or may be substituted, or combinations thereof; or a C5-C18 cycloalkyl which may contain a side group, may contain a bridge, may contain a heteroatom or may be substituted, or a combination thereof;
$R_4$ is H or a C1-C18 alkyl, which may be branched, may contain a heteroatom or may be substituted, or combinations thereof; a C1-C18 alkenyl, which may be branched, may contain a heteroatom or may be substituted, or combinations thereof; a C1-C18 alkynl, which may be branched, may contain a heteroatom or may be substituted, or combinations thereof; a C3-C18 aryl which may contain a side group, may contain a bridge, may contain a heteroatom or may be substituted, or combinations thereof; or a C5-C18 cycloalkyl which may contain a side group, may contain a bridge, may contain a heteroatom or may be substituted, or a combination thereof,
further the envisaged compound inhibits mitochondrial fusion or increases apoptosis.

In a related aspect, such a compound may include, but is not limited to, 2-((E-((E)-2-(2-chlorophenylimino)-4-oxothiazolin-5-ylidene)methyl)-6-ethoxyphenolate and (E)-5-(4-methylbenzylidene)-3-((4-methylpiperidin-1-yl)methyl)-2-thioxothiazolidin-4-one.

In another related aspect, compounds may include, but are not limited to, those selected from (Z)-ethyl-5-benzylidene-2-(4-nitrophenylamino)-4-oxo-tetrahydrothiophene-3-carboxylate, 5-(5-chloro-2(2-(m-tolyloxy)ethoxy)benzylidene)-2-thioxo-dihydropyrimidin-4,6(1H,5H)-dione, and 1-(3-bromophenyl)-3-(ethoxycarbonyl)-2-methyl-1H-benzo[g]indol-5-olate, where the compounds inhibit mitochondrial fusion.

In another embodiment, a compound of the general formula is envisaged:

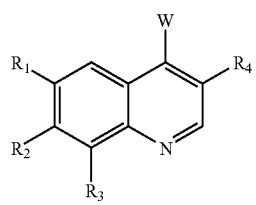

where W is OH or an ester, where said ester may contain a C3-C18 aryl which may contain a side group, may contain a bridge, may contain a heteroatom or may be substituted, or combinations thereof;
$R_1$ is independently H; a C1-C18 alkyl, which may be branched, may contain a heteroatom or may be substituted, or combinations thereof; a C1-C18 alkenyl, which may be branched, may contain a heteroatom or may be substituted, or combinations thereof; a C1-C18 alkynl, which may be branched, may contain a heteroatom or may be substituted, or combinations thereof; a C3-C18 aryl which may contain a side group, may contain a bridge, may contain a heteroatom or may be substituted, or combinations thereof; or a C5-C18 cycloalkyl which may contain a side group, may contain a bridge, may contain a heteroatom or may be substituted, or combinations thereof; or a halogen;
$R_2$ is H; a C1-C18 alkyl, which may be branched, may contain a heteroatom or may be substituted, or combinations thereof; or a halogen;
$R_3$ is H; a C1-C18 alkyl, which may be branched, may contain a heteroatom or may be substituted, or combinations thereof;
$R_4$ is H; a C1-C18 alkyl, which may be branched, may contain a heteroatom or may be substituted, or combinations thereof;
further the envisaged compound causes the formation of net like structures in mitochondria, inhibits mitochondrial fission or inhibits apoptosis.

In a related aspect, such a compound may include, but is not limited to, 6-chloro-4-hydroxy-8-methylquinoline-3-carboxylic acid and 7-chloro-4-(4-chloro-3,5-dimethylphenoxy)quinolone.

In another embodiment, the present invention provides a method of inhibiting mitochondrial fission in a cell, including mammalian cells. The method includes contacting the cell with a compound of the present invention.

In yet another embodiment, the present invention provides a method of inhibiting apoptosis in a cell. The method includes contacting the cell with a compound of the present invention.

In another embodiment, the present invention provides a method of treating a condition associated with apoptosis, wherein the treatment includes decreasing apoptosis. The method includes administering to a subject in need of such treatment a compound of the present invention.

In yet another embodiment, the present invention provides a method for treating a condition associated with apoptosis. The method includes administering to a subject in need of such treatment an agent capable of regulating mitochondrial fission or mitochondrial fusion.

In still another embodiment, the present invention provides a method of treating a condition associated with apoptosis, wherein the treatment includes increasing apoptosis. The method includes administering to a subject in need of such treatment an agent capable of increasing mitochondrial fission or decreasing mitochondrial fusion.

In yet another embodiment, the present invention provides a method of treating a condition associated with apoptosis, wherein the treatment includes decreasing apoptosis. The method includes administering to a subject in need of such treatment an agent capable of decreasing mitochondrial fission or increasing mitochondrial fusion.

In yet another embodiment, the present invention provides a method of screening for an agent capable of decreasing mitochondrial fission. The method includes identifying an agent that suppresses the growth defect of a cell with decreased mitochondrial fusion.

In still another embodiment, the present invention provides a method of screening for an agent capable of increasing mitochondrial fission. The method includes identifying an agent that suppresses the growth on a non-fermentable carbon source of a cell in wild type and does not suppress the growth on a non-fermentable carbon source of the cell defective in mitochondrial fission.

DETAILED DESCRIPTION OF THE INVENTION

The present invention is based, in part, on the discovery that cell death, e.g., apoptosis can be regulated via regulation of mitochondrial fission, mitochondrial fusion, or the balance between the two events. Accordingly the present invention provides compounds capable of regulating mitochondrial fission or fusion and methods of identifying such compounds. In addition, the present invention provides methods of regulating apoptosis or treating conditions associated with apoptosis via regulating mitochondrial fission or fusion events.

Figure 1:
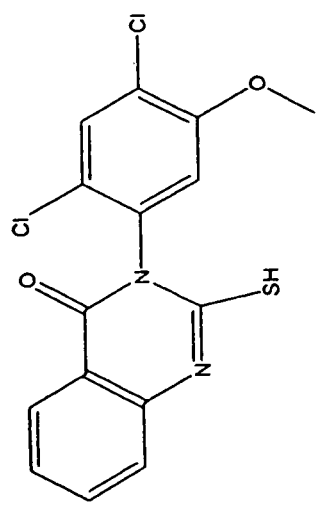
FIG. 1 shows the structures of top three compounds capable of inhibiting mitochondrial fission.
Figure 1:
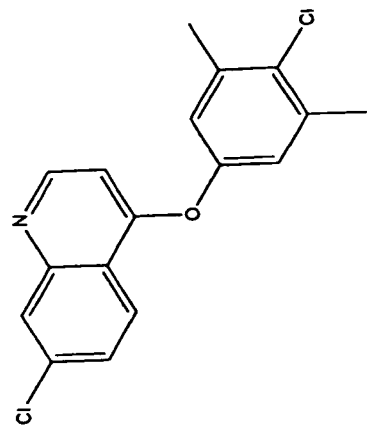
Figure 1:
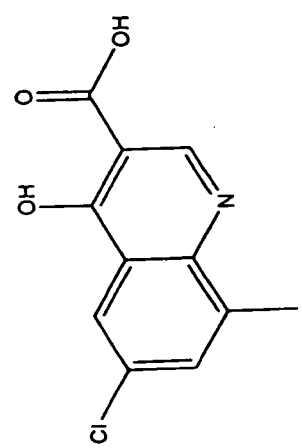

According to one feature of the present invention, it provides compounds that are capable of regulating apoptosis, e.g., via regulating mitochondrial fission or fusion. In one embodiment, the compound provided by the present invention has a formula of Compound A1, Compound B, or Compound C as shown in FIG. 1. The formula of Compound A1, Compound B, or Compound C represents a class of compounds having the core structure as shown in the formula.

In another embodiment, the compound provided by the present invention is a derivative of Compound A1, Compound B, or Compound C. In general, the derivatives of Compound A1, Compound B, or Compound C have the core structure of Compound A1, Compound B, or Compound C and are capable of regulating apoptosis, e.g., via regulating mitochondrial fission or fusion.

In yet another embodiment, the compound provided by the present invention is a derivative of Compound A1. According to the present invention, the derivatives of Compound A1 can be any compound that has a quinazolinone ring and an unblocked sulthydryl as shown in the formula of A1 and a phenyl ring with constituents that are sufficiently bulky to cause the molecule to be an atropisomer due to limited rotation about the nitrogen-phenyl bond, e.g., isomers that can be separated only because rotation about a single bond is prevented or greatly slowed.

The compounds of interest generally are inhibitors. Thus, a compound of interest could be developed as a drug candidate. A compound of interest also could be used to identify other molecules that modulate apoptosis by, for example, competition assays.

The term "alkyl" means a straight or branched chain hydrocarbon. Representative examples are methyl, ethyl, propyl, isopropyl, butyl, isobutyl, tert butyl, sec butyl, pentyl and hexyl. The hydrocarbon can contain one or more unsaturated triple bonds.

The term "alkoxy" means an alkyl group bound to an oxygen atom. Examples are methoxy, ethoxy, propoxy, butoxy and pentoxy.

"Aryl" is a ring which is an aromatic hydrocarbon. Examples include phenyl and naphthyl.

Heteroatom" generally is an atom that differs from those that typify a molecule. Thus, in a hydrocarbon, any atom not a carbon or a hydrogen is a heteroatom. Common biologically acceptable heteroatoms include oxygen, sulfur and nitrogen.

The term "heteroaryl" relates to an aryl group where one or more carbon atoms is replaced with a heteroatom. Examples are pyridyl, imidazolyl, pyrrolyl, thienyl, furyl, pyranyl, pyrimidinyl, pyridazinyl, indolyl, quinolyl, naphthyridinyl and isoxazoyl.

"Branched" means the structure contains one or more branches at one or more sites. A branch can be an R group as defined above or other side group.

The term "cycloalkyl" refers to a cyclic hydrocarbon. Some examples are cyclopropyl, cyclobutyl, cyclopentyl and cyclohexyl. May contain a bridge of varying length.

"Heterocycle" is a cycloalkyl where one or more carbon atoms are replaced with a heteroatom. Examples are pyrrolidinyl, piperidinyl and piperazinyl.

The term "heteroalkyl" is an alkyl where one or more carbon atoms are replaced with a heteroatom. An ether is a heteroalkyl.

By "substituted" is meant that the base organic radical has one or more substituent groups. Thus, an atom or group replaces another atom or group in a molecule. Representative substituents include a halogen, C1-C8 alkyl, —CN, alkoxyl, hydroxyl, sulfide, sulfate, sulfonamide, amine, amide, an alcohol, a keto group, C6-C18 aryl, a halogenated C1-C18 alkyl, a nitrite group or a nitrate group.

A "halogen" is, for example, chlorine, fluorine or bromine.

An "alkenyl" is a hydrocarbon containing one or more carbon-carbon double bonds. The hydrocarbon can be branched.

The term "ring" means one, one of a plurality of ring structures or a plurality of ring structures, where two or more of the plurality of rings can be fused, wherein the or one or more of the plurality of rings may be aromatic, contain a heteroatom, may be substituted or a combination thereof. The ring may be bicyclic or polycyclic. The ring may contain a bridge of varying length.

The term "side group" means an atom or molecule attached to another structure. Thus, a side group can be an R group defined above, an alkyl, an aryl, a cycloalkyl and so on.

The term "bridge" refers to a linker between two structures. For example, a non-cyclic hydrocarbon, such as an alkyl, alkenyl and the like, which can contain a heteroatom, can be substituted, can be branched or combinations thereof, can connect two cyclic hydrocarbons, such as aryl or cycloalkyl groups. The bridge also may be contained within a cyclic structure joining at least two atoms of the cyclic structure. The intramolecular bridge may contain 0, 1, 2, 3, 4 or more atoms. The intramolelcular bridge may be linear, branched and contain substitutions.

The compounds of interest contain functional groups that can be derivatized to form prodrugs to enhance bio-availability. Thus, the instant invention contemplates variants of the active compounds of interest that following administration, are metabolized to a bioactive form. Such bioactive drug precursors are also known as bioreversible carriers, latent drugs, drug delivery systems or prodrugs. ("Bioreversible Carriers in Drug Design" E. B. Roche, ed., Pergamon, N.Y., 1987; "Prodrugs as Novel Drug Delivery Systems", Higuchi & Stella, eds., American Chemical Society, DC, 1975)

Chemical modification of drugs is directed to address particular aspects of pharmacodynamics, such as how to enhance availability of a polar compound that must cross a lipid barrier, how to stabilize a compound normally susceptible to degradation in vivo and so on.

Other reasons to make prodrugs include bioactive drug toxicity, lack of specificity, instability, being metabolized at the absorption site, being absorbed too quickly, patient compliance, such as poor taste or pain at injection site, poor doctor acceptance or formulation problems as well.

A common modification is esterification, which is not limited to derivation of a carboxyl group. Chemistry exists for making such derivatives, for example, for amines, imines, sulfur containing substituents and amides as well.

In the case of esters, various substituents can be added thereto, including unbranched, cyclic or branched hydrocarbons that can be substituted, can contain one or more double or triple bonds, can contain ring structures, the hydrocarbon backbone can contain one or more heteroatoms, such as nitrogen, sulfur or oxygen, and so on.

When considering the R group for constructing the ester, another factor to consider is the susceptibility of enzymic cleavage. Thus, steric charge and conformational factors can be determinative for bioavailability. For example, a branched alkyl group may provide steric hindrance for accessibility to the esterase active site, thereby slowing the rate of hydrolysis. That either may be less desirable, bioavailability is delayed, or desirable, bioavailability is prolonged.

In other circumstances, it is desirable to enhance aqueous solubility of a drug. Examples of substituents that achieve that goal include succinates, sulfates, hemisuccinates, phosphates, amino acids, acetates, amines and the like.

Nitrogens of amides, imides, carbonates, hydrantoins and the like can be derivatized. Suitable groups for reaction to the nitrogen include hydroxymethyl groups, or hydroxyalkyl groups in general, acyloxyalkyl groups and acyl groups.

Carbonyl groups also are sites for derivation. Examples of derivatives are Schiff bases, oxines, ketals, acetals, oxazolidines, thiazolidines and enol esters.

While the derivatives discussed above comprise covalent bonding of the substituent to the drug, a substituent may be attached to the drug in other ways, for example, hydrogen bonding, van der Waals forces, electrostatic forces, hydrophobic interactions and the like.

Yet another means of derivatization is to use substituents that are removed from a prodrug by a nonenzymatic mechanism. Examples include prodrugs that contain (2 oxo-1,3-dioxol-4-yl)methyl esters, Mannich bases, oxazolidines, esters with a basic side chain that catalyze intramolecular hydrolysis and esters or amides that undergo an intramolecular nucleophilic cyclization elimination reaction. The cyclization mechanism is available for drugs containing phenols, alcohols and amines. "Prodrug Design" Testa & Mayer in "Encyclopedia of Pharmaceutical Technology," 2nd ed. V. 3, Swarbrick & Boylan, eds., Marcel Dekker, 2002.

Therefore, the instant invention contemplates any further modification of the compounds of interest practicing known synthesis methods to obtain compounds that once administered react or are acted on in vivo to yield a compound that modulates apoptosis in a cell.

The compounds provided by the present invention usually can be provided as a pharmaceutical composition including one or more compounds of the present invention and a pharmaceutically acceptable carrier. Pharmaceutically acceptable carriers are well known to those in the art. Such carriers include, without limitation, large, slowly metabolized macromolecules, e.g., proteins, polysaccharides, polylactic acids, polyglycolic acids, polymeric amino acids, amino acid copolymers, and inactive virus particles.

Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, e.g., water, saline, glycerol, and ethanol, as well as substances, e.g., wetting agents, emulsifying agents, or pH buffering agents. In addition, liposomes or other delivery particles can also be used as a carrier for the compositions of the present invention.

Typically, the compounds of the present invention are prepared or formulated in general as an injectable, either as a liquid solution or suspension. However, solid forms suitable for solution in, or suspension in, liquid vehicles prior to injection can also be prepared. The compounds of the present invention can also be formulated into an enteric-coated tablet or gel capsule according to known methods in the art.

The compounds provided by the present invention can be used to regulate mitochondrial fission or fusion in vivo or in vitro, e.g., via contacting a cell with the compounds provided by the present invention. The compounds provided by the present invention can also be used to regulate cell death, e.g., apoptosis in vivo or in vitro, e.g., via contacting a cell with the compounds provided by the present invention.

In one embodiment, the compounds provided by the present invention, e.g., compounds capable of inhibiting mitochondrial fission can be used to treat conditions associated with apoptosis, especially in treatments involving inhibition of or decreasing apoptosis. For example, in various conditions it is desirable to decrease or suppress apoptosis in order to limit cell or tissue damage. Such conditions usually are associated with chronicle or acute cell death associated with toxicity or lack of oxygen or blood supply to cells or tissues, e.g., Parkinson's disease, ALS, stroke, heart attack, congestive heart failure, transplantation, alcoholic hepatitis, and drug induced liver toxicity.

In another embodiment, the compounds provided by the present invention, e.g., compounds capable of inhibiting mitochondrial fusion can be used to treat conditions associated with apoptosis, especially in treatments involving increasing apoptosis. For example, in various conditions it is desirable to increase or promote apoptosis in order to increase cell death associated with undesirable growth. Such conditions usually are associated with neoplasia, cancer, tumor, etc.

The compositions of the present invention useful for therapeutic treatment can be administered alone, in a composition with a suitable pharmaceutical carrier, or in combination with other therapeutic agents. An effective amount of the compositions of the present invention to be administered can be determined on a case-by-case basis. Factors should be considered usually include age, body weight, stage of the condition, other disease conditions, duration of the treatment, and the response to the initial treatment.

The compositions of the present invention may be administered in any way which is medically acceptable which may depend on the disease condition or injury being treated. Possible administration routes include injections, by parenteral routes such as intravascular, intravenous, intraepidural or others, as well as oral, nasal, ophthalmic, rectal, topical, or pulmonary, e.g., by inhalation. The compositions of the present invention may also be directly applied to tissue surfaces, e.g., during surgery. Sustained release administration is also specifically included in the invention, by such means as depot injections or erodible implants.

According to another feature of the present invention, it provides methods for treating a condition associated with apoptosis including administering to a subject in need of such treatment an agent capable of regulating mitochondrial fission or fusion. In one embodiment, treating a condition associated with apoptosis involves increasing apoptosis, e.g., cancer and the method provided by the present invention includes administering to a subject in need of such treatment an agent capable of increasing mitochondrial fission or decreasing mitochondrial fusion.

In another embodiment, treating a condition associated with apoptosis involves decreasing apoptosis, e.g., limiting cell or tissue damage and the method provided by the present invention includes administering to a subject in need of such treatment an agent capable of decreasing mitochondrial fission or increasing mitochondrial fusion.

According to yet another feature of the present invention, it provides methods of screening for an agent capable of regulating mitochondrial fission or fusion. In one embodiment, the present invention provides a method of screening for an agent capable of decreasing mitochondrial fission or increasing mitochondrial fusion, which includes identifying an agent that suppresses the growth defect of a cell with defective mitochondrial fusion.

For example, a cell containing a conditional mutation, e.g., temperature sensitive mutation for blocking mitochondrial fusion develops fragmentation in mitochondrial membranes under non-permissive condition and a secondary consequence of such fragmentation is loss of mtDNA and inability for the cell to grow on non-fermentable carbon sources, e.g., glycerol. According to the present invention, any agent, e.g., compound that suppresses or decreases such growth defect is an agent capable of suppressing or decreasing mitochondrial fission.

In another embodiment, the present invention provides a method of screening for an agent capable of increasing mitochondrial fission or decreasing mitochondrial fusion, which includes identifying an agent that suppresses or decreases the growth on a non-fermentable carbon source of a wild type cell while does not suppress or decreases the growth of a cell defective in mitochondrial fission.

For example, to identify an agent capable of activating or increasing mitochondrial fission or inhibiting or decreasing mitochondrial fusion, one can screen for compounds that inhibit the growth of wild type cells on non-fermentable carbon source, but do not inhibit growth of cells with defective mitochondrial fission, e.g., dnm1 mutant cells. By comparing the effects of compounds on wild type versus mitochondrial fission mutant, e.g., dnm1 mutant cells, one can identify agents capable of inhibiting mitochondrial fusion or activating mitochondrial fission.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Mitochondrial Fission is a Regulated, Multi-step Process Controlled by the Dynamin-related GTPase, Dnm1p Mitochondrial fission in yeast is mediated by Drn1p, which is localized primarily in the form of assembled punctate structures in the cytosol and on the cytosolic face of the mitochondrial outer membrane (Bleazard et al., 1999 *Nature Cell Biology* 1, 298-304, Sesaki et al., 1999 *Journal of Cell Biology* 147, 699-706.). On mitochondria, these Dnm1p-containing puncta are directly associated with sites of mitochondrial constriction and fission. Dnm1p is a GTPase structurally related to dynamin, a protein required during endocytosis for the formation and scission of clathrin-coated vesicles from the plasma membrane. Deletion of DNM1 in yeast causes mitochondria to form net-like structures of interconnected mitochondrial tubules in cells (Bleazard et al., 1999 *Nature Cell Biology* 1, 298-304, Sesaki et al., 1999 *Journal of Cell Biology* 147, 699-706.) These net-like mitochondrial structures arise in dnm1 cells because tubule ends cannot be generated by mitochondrial division and fusion continues unopposed.

The higher eucaryote homolog, Drp1, also has been shown to control mitochondrial fission, indicating that the mechanism of this process is evolutionarily conserved (Smirnova et al., 2001 *Mol Biol Cell* 12, 2245-56.). Mitochondrial fission has been observed to occur during apoptosis and has been shown to be required for this process. Recently, the Bcl-2 proapoptotic mitochondrial associated protein, Bax, was shown to co-localize with Drp1 and the mitochondrial fusion-promoting protein, Mfn2, suggesting that Bax may interact with the fission and fusion machinery to promote apoptosis (Karbowski et al., 2002 *J Cell Biol* 159, 931-8.).

From genetic screens in yeast, we know that at least two additional components are required for fission: the WD repeat protein, Mdv1p and the mitochondrial integral outer membrane protein, Fis1p (Tieu et al., 2000 *The Journal of Cell Biology* 151, 353-365, Mozdy et al., 2000 *Journal of Cell Biology* 151, 367-379.). Our genetic, biochemical and cytological studies suggest a model for mitochondrial fission where Dnm1p self-assembles into punctate structures that are targeted to the mitochondrial membrane in a manner dependent on Fis1p (Tieu et al., 2000 *The Journal of Cell Biology* 151, 353-365, Tieu et al., *Journal of Cell Biology* 158, 445-452.). Once targeted to the mitochondrial membrane, Mdv1p assembles into Drn1p-containing structures and together with Fis1p facilitates Dnm1p-dependent mitochondrial fission. We also have further defined the role of Mdv1p in fission by examining the structural features of Mdv1p required for its interactions with Dnm1p and Fis1p (Tieu et al., Journal of Cell Biology 158, 445-452.). Data from two-hybrid analyses and GFP-tagged domains of Mdv1p indicate that it contains two functionally distinct domains separated by a central coiled-coil region. We believe that this structure enables Mdv1p to function as an oligomeric molecular adaptor that regulates sequential interactions between Dnm1p and Fis1p during the rate-limiting step of mitochondrial fission.

Using a combination of approaches, including the chemical genetic approach outlined here, we are now be able to understand how Dnm1p, Fis1p and Mdv1p assemble together to cooperatively generate the force required to constrict and ultimately divide the outer and inner mitochondrial membranes. We also are also able to shed light on the controversial issue of whether dynamin-related GTPases function as force generating or classical GTPases in cellular trafficking (Sever et al., 2000 *Traffic* 1, 385-392.). We can determine how the rate of mitochondrial fission is regulated in cells with the goal of understanding the physiological significance of the range of mitochondrial morphologies observed in different cell types and the role of membrane dynamics in apoptosis.

Example 2

Mitochondrial Fusion also Requires a Dynamin-related GTPase, Mgm1p, which is Part of a Complex that Spans the Mitochondrial Outer and Inner Membranes The coordinated fusion of the mitochondrial outer and inner membranes requires the evolutionarily conserved fuzzy onions (Fzo) family of mitochondrial outer membrane GTPases (Hales et al., 1997 *Cell* 90, 121-129, Hermann et al., 1998 *The Journal of Cell Biology* 143, 359-374, Santel et al., 2001 *J Cell Sci* 114, 867-74.) In *Drosophila*, mutations in Fzo block a developmentally-regulated mitochondrial fusion event during spermatogenesis (Hales et al., 1997 *Cell* 90, 121-129.) Previous work revealed that the yeast ortholog of fuzzy onions, Fzo1p, plays a direct and conserved role in mitochondrial fusion (Hermann et al., 1998 *The Journal of Cell Biology* 143, 359-374.).

We observed that at non-permissive temperatures a conditional fzo1 mutation causes mitochondria to fragment, a phenotype consistent with ongoing mitochondrial fission and a block in mitochondrial fusion. To establish that Fzo1p is required for mitochondrial fusion, we used an assay to directly monitor mitochondrial fusion in yeast cells during mating (Nunnari et al., 1997 *Molecular Biology of the Cell* 8, 1233-1242.) We observed that mitochondrial fragments fail to fuse in fzo1 zygotes formed under non-permissive conditions, providing a direct demonstration that Fzo1p mediates an essential step in this process.

In addition, although mitochondrial tubules normally fragment at non-permissive temperature in fzo1-1 cells, fragmentation is blocked and mitochondria remain tubular in cells that also are defective in mitochondrial fission (i.e. fzo1-1/Δdnm1 double mutant). This result indicates that mitochondrial fragmentation in fzo1-1 cells is the result of unopposed mitochondrial fission, confirming our model that a balance between fission and fusion is required for the maintenance of normal mitochondrial morphology. Using similar approaches, another integral outer membrane, Ugo1p, was shown to be required for mitochondrial fusion (Sesaki et al., 2001 *J Cell Biol* 152, 1123-34.).

Interestingly, mutations in a second mitochondrial-associated dynamin-related GTPase, Mgm1p, produce similar phenotypes to fzo1 and ugo1 cells. Specifically, mutations in MGM1 cause fragmentation and aggregation of mitochondria with secondary loss of mtDNA, raising the possibility that MGM1 might function in fusion (Shepard et al., 1999 *Journal of Cell Biology* 144, 711-719, Wong et al., 2000 *The Journal of Cell Biology* 151, 341-352.) Consistent with this, mitochondrial fragmentation and mtDNA loss in mgm1 mutants is suppressed when fission is abolished by deletion of DNM1 and blocking DNM1-dependent fission in mgm1 null cells does not restore mitochondrial fusion during mating.

We have characterized the role of Mgm1p in fusion by testing for molecular interactions with known fusion components and have demonstrated that Mgm1p is associated with both Ugo1p and Fzo1p in mitochondria. In addition, genetic analysis of specific mgm1 alleles indicates that Mgm1p self-interacts, suggesting that it functions in fusion as a self-assembling GTPase.

Mgm1p's localization within mitochondria has been controversial (Shepard et al., 1999 *Journal of Cell Biology* 144, 711-719, Wong et al., 2000 *The Journal of Cell Biology* 151, 341-352, Pelloquin et al., 1999 *Journal of Cell Science* 112, 4151-4161.). Using protease protection and immuno-EM, we previously showed that Mgm1p localizes to the intermembrane space, associated with the inner membrane. To further test our conclusions, we have used a novel method employing the TEV protease, and confirm that Mgm1p is present in the intermembrane space compartment in vivo.

Recently, the human homolog of Mgm1p, OPA1, was shown to be mutated in individuals with autosomal dominant optic atrophy and mutations in OPA1 have been observed to cause defects in mitochondrial morphology, similar to those observed in mgm1 cells (Delettre et al., 2000 *Nature Genetics* 26, 207-210, Alexander et al., 2000 *Nature Genetics* 26, 211-215.) These findings indicate that the mechanism of mitochondrial fusion is conserved in eucaryotes.

Our data provide a model where the intermembrane space protein Mgm1p functions in fusion as a self-assembling GTPase and plays a role in coordinating the inner and outer membranes during the fusion process. As a self-assembling GTPase, Mgm1p can directly promote the fusion of the inner membrane by helping to form a transient tubule or protrusion of this membrane, similar to the role proposed for the dynamin-related GTPase, phragmoplastin in cell plate formation in plants. This Mgm1p-dependent inner membrane remodeling event can be regulated by fusion-promoting events in the outer membrane via Mgm1p's interaction with Ugo1p and Fzo1p. In addition, Mgm1's interactions with Ugo1p and Fzo1p may serve to physically coordinate the behavior of both membranes and promote the formation of a double membrane structure with a higher radius of curvature, thereby producing a fusion competent micro-environment. Alternatively, Mgm1p can function as a classical GTPase that recruits Fzo1p and Ugo1p, which in turn promote fusion, similar to the role proposed for dynamin during endocytosis.

Example 3

Screening Strategy for Compounds that Specifically Affect Mitochondrial Fission and Fusion Primary screens: To increase the chances of drug uptake of yeast cells, null mutations in the PRD1 and PRD3 genes, which encode for multi-drug resistance transporters were created in the various strains used in our screens. These additional mutations have no affect on mitochondrial dynamics in cells. Compounds are routinely screened at 50-100 µM.

As stated above, the temperature-sensitive fzo1-1 allele blocks mitochondrial fusion at the non-permissive temperature of 37° C., causing mitochondrial membranes to fragment. As a secondary consequence of this fragmentation, fzo1-1 mitochondria lose mtDNA and cells are unable to grow on the non-fermentable carbon source glycerol, but cells can still be propagated if grown using a fermentable carbon source, such as glucose. Mutations in components required for fission, such as DNM1, suppress mitochondrial fragmentation and mitochondrial DNA loss in fzo1-1 cells and thus suppress the glycerol growth defect at non-permissive temperatures (fzo1-1 dnm1). Surprisingly in yeast, loss of mitochondrial fission has no associated growth phenotype under laboratory conditions.

Based on these observations, to identify compounds that inhibit fission/activate fusion we have screened for compounds that suppress the glycerol growth defect of fzo1-1 cells at 37° C. To identify compounds that inhibit fusion/activate fission, we have screened for compounds that inhibit the growth of wild type cells on glycerol, but do not inhibit growth of dnm1 mutant cells, defective in mitochondrial fission. Comparing the effects of compounds on wild type versus dnm1 mutant cells will identify drugs that cause mtDNA loss that is suppressed by abolishing mitochondrial fission—the identical phenotype of fusion defective cells.

Secondary screens: Compounds identified in the primary growth assay-based screens outlined above are screened secondarily by examining their effects on mitochondrial morphology. We use the steady state structure of mitochondria as an indicator of the relative rates of mitochondrial fission and fusion in cells. We assay for morphological phenotypes and quantify the percentage of cells that possess a given morphology (i.e. tubular, fragmented, net-like). Mitochondria are visualized using a mitochondrial targeted GFP that is efficiently targeted to both wild type and respiratory deficient mitochondria (Tieu et al., 2000 *The Journal of Cell Biology* 151, 353-365.).

To distinguish whether compounds specifically affect mitochondrial fission or fusion, we directly measure the rates of these events by examining the behavior of mitochondria using time-lapse fluorescence microscopy after drug addition. We routinely perform this type of experiment using a DeltaVision deconvolution microscope.

Screen Data:

We have screened representative member compounds from several commercially available combinatorial libraries for small molecules that affect mitochondrial fission and fusion. Table 1 displays data from a portion of our screen for inhibitors of fission.

TABLE 1

Summary of screen for compounds that block fission/activate fusion

| Library name | Library size | # primary growth screen | # secondary morphology screen |
|---|---|---|---|
| NCI Diversity | 1900 compounds | 6 | 0 |
| Peakdale | 2800 compounds | 0 | 0 |
| Bionet | 4800 compounds | 16 | 2 |
| Cerep | 4800 compounds | 6 | 1 |
| Maybridge | 8800 compounds | 42 | 3 |

As shown in Table 1, a fraction of compounds that screened positive in our primary screen also caused defects in mitochondrial morphology in wild type cells in the secondary screen. Specifically, in all cases, mitochondria formed net-like structures in a significant fraction of treated cells, similar to those observed in cells defective for mitochondrial fission. Preliminary dose-response analysis of these compounds revealed top three compounds, Compound A1, Compound B, and Compound C as shown in FIG. 1. The efficacy of each compound in inhibiting mitochondrial fission is shown in Table 2.

TABLE 2

Mitochondrial Morphology after Drug is Added

| cpd | Reticular | Fragmented | Nets |
|---|---|---|---|
| A1 | .40 | .05 | .55 |
| B | .70 | .10 | .20 |
| C | .85 | .04 | .11 |

The most efficacious compound, Compound A1, is a derivative of quinazolinone and causes net-like mitochondria to form in wild type cells within 1 minute after addition at sub-µM concentrations.

Compound analysis: We have performed detailed structure-function analysis on the quinazolinone derivative. We have made compounds that are structurally similar to compound A1 and tested their ability to inhibit mitochondrial fission.

TABLE 3

Structure Function Analysis of Compound A1

| Structure | % reticular | % fragmented | % nets |
|---|---|---|---|
| (quinazolinone structure) | 63 | 8 | 29 |

TABLE 3-continued

Structure Function Analysis of Compound A1

| Structure | % reticular | % fragmented | % nets |
|---|---|---|---|
| (structure) | 82 | 11 | 7 |
| (structure) | 89 | 6 | 5 |
| (structure) | 87 | 8 | 5 |
| (structure) | 48 | 51 | 1 |
| (structure) | 91 | 8 | 1 |
| (structure) | 94 | 6 | 0 |
| (structure) | 100 | 0 | 0 |
| (structure) | 68 | 32 | 0 |
| (structure) | 31 | 69 | 0 |
| (structure) | 96.8 | 3.2 | 0 |
| (structure) | 92.7 | 7.3 | 0 |

Figure 2:
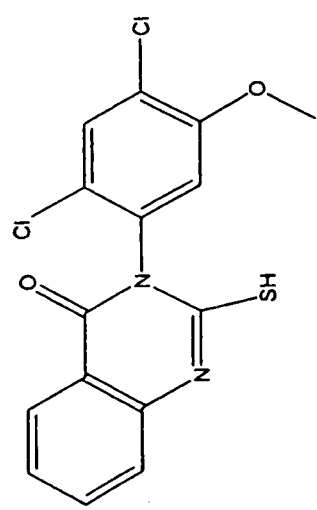
FIG. 2 shows the structure function analysis of compound A1.
Figure 2:
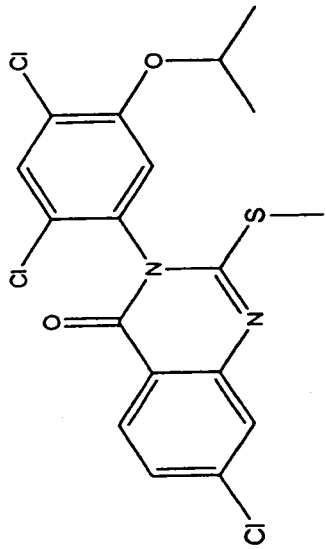
Figure 2:
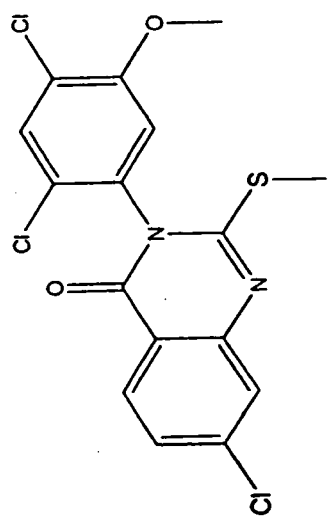

Specifically, we have compared the functions of Compound A1, A2, and A3 as shown in FIG. 2. Table 4 summaries the data on the efficacy of each in inhibiting mitochondrial fission, which is indicated by net formation.

TABLE 4

Structure Function Analysis of A1, A2, and A3.

| cpd | Reticular | Fragmented | Nets |
|---|---|---|---|
| A1 | .40 | .05 | .55 |
| A2 | .92 | .01 | .07 |
| A3 | .87 | .12 | .01 |

Figure 3:
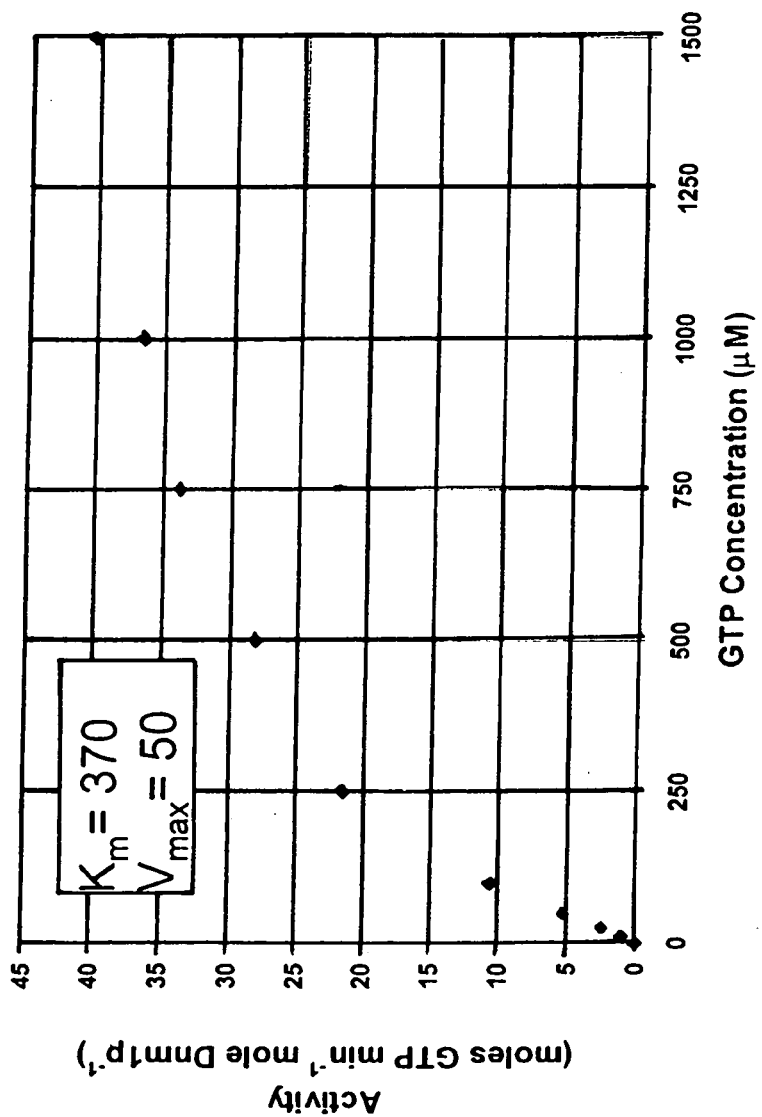
FIG. 3 shows the GTPase activity of recombinant Dnm1 purified from baculovirus-infected insect cells.
Figure 4:
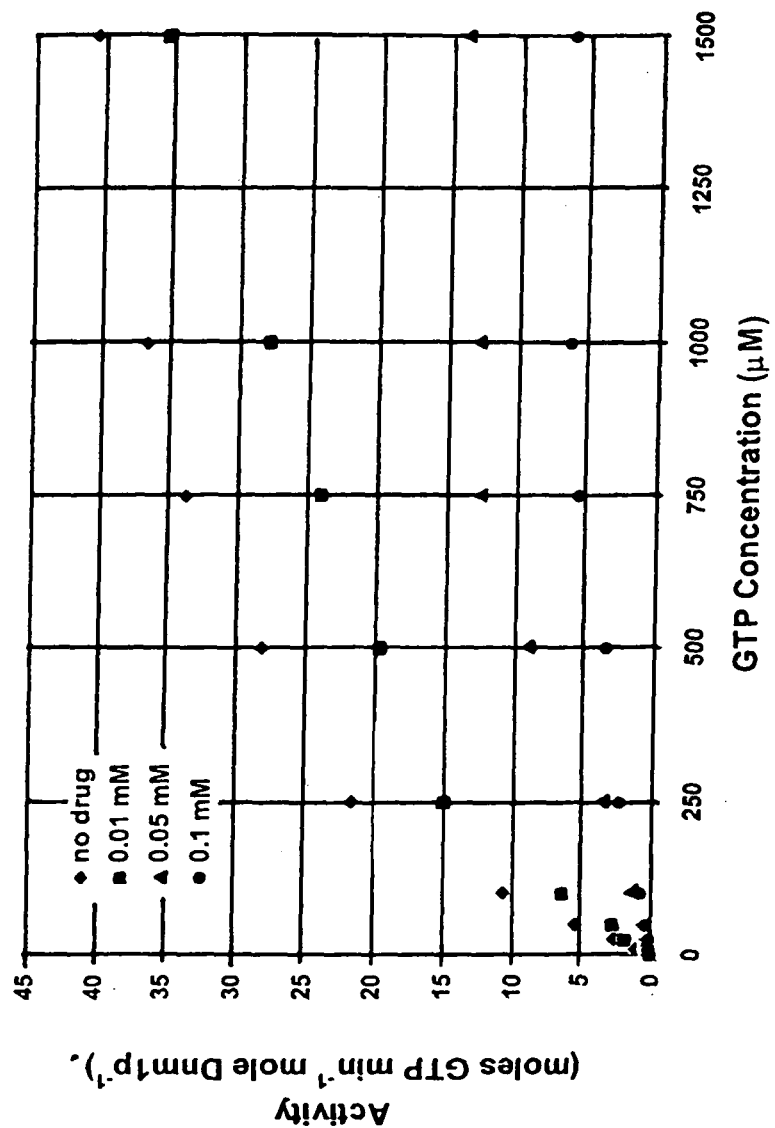
FIG. 4 shows the kinetic analysis of recombinant Dnm1 GTPase activity at different concentrations of compound A1.
Figure 5:
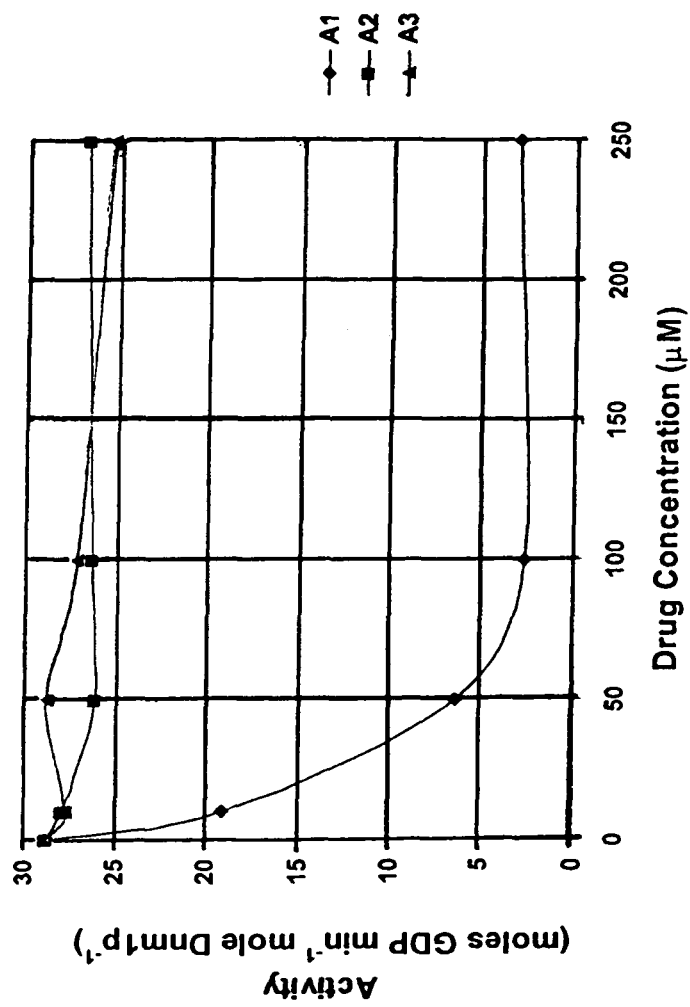
FIG. 5 shows the Dnm1 dose-response curves for compounds A1, A2 and A3.

FIG. 3 demonstrates the GTPase activity of recombinant Dnm1 at various concentrations of compound A1, while FIG. 4 shows the kinetic analysis of recombinant Dnm1 GTPase activity at different concentrations of compound A1. FIG. 5 shows the Dnm1 dose-response curves for compounds A1, A2, and A3. Compounds A2 and A3 which are structurally similar to compound A1 do not inhibit recombinant Dnm1 GTPase activity.

We also have determined that the target of this compound is the dynamin-related GTPase, Dnm1, which is the master regulator of mitochondrial fission. In addition, we have shown that this, and other compounds that block mitochondrial fission in vivo in yeast, also can block mitochondrial fission in mammalian COC cells in culture, as indicated by changes in mitochondrial morphology upon drug addition.

Example 4

Identification of Inhibitors of Mitochondrial Fission and Fusion

Figure 6:
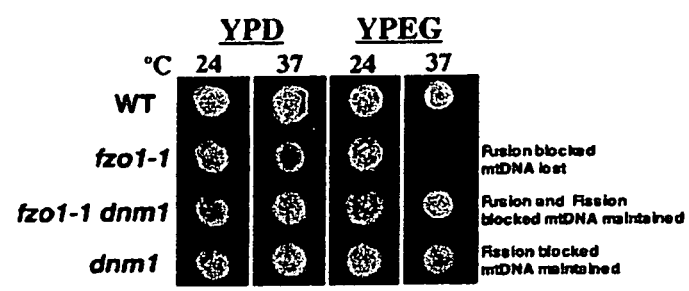
FIG. 6 shows growth phenotypes of yeast mitochondrial fission and fusion-defective mutants.

We have identified small molecules that inhibit or activate mitochondrial fission and fusion by high-throughput screening of chemical libraries using straightforward growth-based assays in *S. cerevisiae* strains engineered so that growth reports on mitochondrial dynamics. To increase the chances of drug uptake in yeast cells, null mutations in the PDR1 and PDR3 genes, which encode for transcriptional regulatory proteins that positively control the expression of multi-drug resistance ABC transporters, were created in the various strains used in our screens and in the analysis of small molecules. These additional mutations have no effect on mitochondrial fission and fusion in cells. Small molecules were routinely screened at single concentrations between 10-100 µM in primary and secondary assays due to the limited amount of the compounds obtained. The solvent used to solubilize the small molecules is DMSO, which to date when tested alone has had no significant effects in any of our assays. Prior to their detailed characterization in the assays described in this grant, all small molecules identified using our screens were and will be authenticated by mass spectrometry Description of Primary and Secondary Screens To identify inhibitors of mitochondrial fission, we exploited the growth phenotypes of mitochondrial fission and fusion-defective mutants. Yeast cells harboring the temperature-sensitive fzo1-1 allele, which causes mitochondrial membranes to fragment under non-permissive conditions lose mtDNA, and are unable to grow on the non-fermentable carbon source glycerol (FIG. 6, YPEG, 37° C.). These cells can still be propagated if grown using a fermentable carbon source, such as glucose (FIG. 6, YPD, 37° C.). Mutations in components required for fission, such as DNM1, suppress mitochondrial fragmentation and mitochondrial DNA loss in fzo1-1 cells and thus suppress the glycerol growth defect at non-permissive temperatures (FIG. 6, fzo1-1 dnm1). In yeast, loss of mitochondrial fission has no associated growth phenotype under laboratory conditions (FIG. 6, dnm1).

Based on these observations, we identified small molecules that potentially inhibit fission/activate fusion by screening for those that suppressed the glycerol growth defect of fzo1-1 cells at 37° C. In other words, we identified small molecules that phenocopy fzo1-1 dnm1 cells, in which both fission and fusion are blocked. To identify small molecules that potentially inhibit fusion/activate fission, we screened for those that inhibited the growth of wild type cells on glycerol, but did not inhibit growth of mitochondrial fission defective dnm1 mutant cells on glycerol. By comparing the effects of compounds on wild type versus dnm1 mutant cells, we identified small molecules that phenocopy fusion defective cells which exhibit mtDNA loss that is suppressed by abolishing mitochondrial fission.

Figure 7:
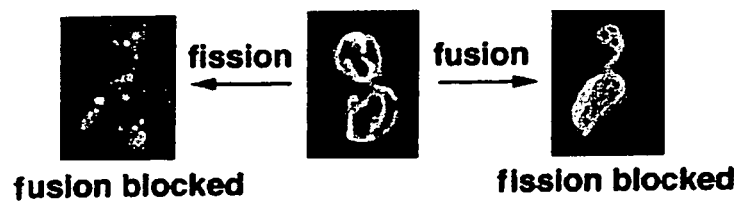
FIG. 7 shows that balanced fission and fusion events determines mitochondrial structure in yeast.

All compounds identified in the primary growth assay-based screens outlined above were screened secondarily by examining their effects on mitochondrial morphology in yeast. From previous work, we know that the steady state structure of mitochondria is an indicator of the relative rates of mitochondrial fission and fusion in cells (FIG. 7). Specifically, net-like structures indicate a block in fission, and fragmented mitochondrial structures indicate a block in fusion. We assayed for morphology phenotypes and quantified the percentage of cells that possess a given morphology (i.e. tubular, fragmented, net-like) using a mitochondrial targeted GFP that is efficiently targeted to both wild type and respiratory deficient mitochondria. In this secondary assay, small molecules were judged to be a hit if they produced a mutant phenotype in greater than 5% of the cell population.

Results from Screens

To date, we have screened representatives from several commercially available libraries for small molecules that affect mitochondrial membrane dynamics (Tables 1 and 2).

TABLE 1

Fission Inhibitor Screen Results

| Library | Library size | Hits 1° Assay | Hits 2° Assay |
|---|---|---|---|
| NCI Diversity | 1,900 | 6 | 0 |
| Peakdale | 2,800 | 0 | 0 |
| Bionet | 4,800 | 16 | 2 |
| Cerep | 4,800 | 3 | 1 (mfisi-1) |
| Maybridge | 8,800 | 42 | 3 |
| Total | 23,100 | 67 (.003) | 6 (.0003) |

TABLE 2

Fusion Inhibitor Screen Results

| Library | Library size | Hits 1° Assay | Hits 2° Assay |
|---|---|---|---|
| NCI Diversity | 1,900 | 0 | 0 |
| Peakdale | 2,800 | 0 | 0 |
| Bionet | 4,800 | 6 | 2 |
| Cerep | 4,800 | 3 | 2 |
| Maybridge | 8,800 | 22 | 10 |
| ChemDiv | 29,000 | 54 | 23 |
| KnownBioactives | 1,040 | 1 | 0 |
| Total | 52,100 | 86 (.0017) | 37 (.0007) |

Figure 8:
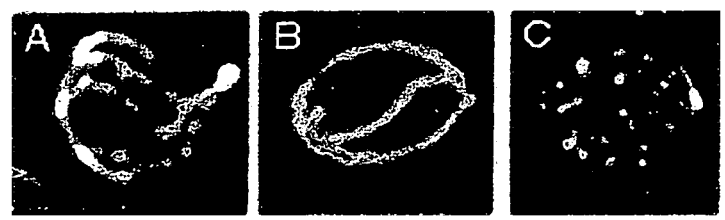
FIG. 8 shows effects on small molecules identified in screen for fission and fusion inhibitors on yeast mitochondrial morphology.

Small molecules were screened using an automated robot to pin transfer compounds to 384-well plates containing yeast strains. Growth was monitored by visual inspection after one, two, and three days. A small fraction of the total compounds screened positive in our primary growth-based screen for mitochondrial fission (Table 1) and fusion (Table 2) inhibitors. Not surprisingly, only a fraction of these compounds were positive in our secondary screen in that they caused mitochondrial morphology defects that phenocopied either mitochondrial fission or fusion defective mutants in wild type cells. FIG. 8 shows the effects of representative small molecules obtained from our fission screens for fission (FIG. 8A) and fusion (FIG. 8C) inhibitors on mitochondrial morphology. The overall frequency of hits using our screens for fission and fusion inhibitors was extremely low (Tables 1 and 2), indicating that our screening strategy is selective.

Prioritization of Small Molecules for Further Analysis

To help prioritize the three potential inhibitors of fission, whose structures are shown in FIG. 9A, dose-response analysis of mitochondrial net-like structure formation in wild type cells was performed. Of the three inhibitors, termed mfisi-1, mifi-2, and mfisi-3 for (for mitochondrial fission inhibitor), the most efficacious is a derivative of quinazolinone (FIG. 9A, mfisi-1), which causes the formation of net-like mitochondria in the majority of wild type cells within minutes after addition with an $IC_{50}$ of approximately 10-20 µM (FIG. 9B). Given its potency and efficacy in comparison with the other two small molecules (mfisi-2 $IC_{50}$, % net=; mfisi-3 $IC_{50}$=, % net=), we have pursued the characterization of this quinazolinone with the highest priority. We have termed this small molecule mfisi-1. In contrast to potential small molecule inhibitors of mitochondrial fission, we identified a greater number of potential inhibitors of mitochondrial fusion, in part because we screened a greater number of small molecules in our primary assay (Table 2).

General Characterizations of mfisi-1

Formally, the small molecules we identified could produce their phenotypes by either inhibiting or activating fission or fusion. To distinguish the exact effects of mfisi-1 and other small molecules identified in our screens on mitochondrial dynamics, we have directly measured the rates of fission and fusion events after drug addition in yeast cells by examining the behavior of mitochondria using time-lapse fluorescence microscopy. Time-lapse analysis of mfisi-1 treated cells indicates that no detectable fission events were observed, but that fusion events occurred. In contrast, in DMSO treated control cells, both fission and fusion events were easily detected in the same time frame. This analysis suggests that mfisi-1 suppresses the glycerol growth defect of fzo1-1 cells and produces mitochondrial net-like structures in wild type cells from its ability to inhibit mitochondrial fission rather than to activate mitochondrial fusion. In addition, mfisi-1 did not change the net-like morphology of mitochondria in Δdnm1 cells, further suggesting that it blocks fission by acting in the Dnm1-dependent fission pathway.

To help determine the specificity of mfisi-1 effects on mitochondrial fission, we examined its effect on two structures in the cell, which when perturbed have been shown to cause indirect changes in mitochondrial morphology: the actin cytoskeleton and the peripheral ER network. These structures are routinely examined in yeast mitochondrial morphology mutants as a test for the specificity of the mitochondrial phenotype. Treatment of cells with 100 μM mfisi-1 caused the formation of mitochondrial net-like structures, but did not result in significant changes in either the actin cytoskeleton or the peripheral ER network (100%, n=50), as compared to control DMSO-treated cells. In contrast, addition of the F-actin depolymerizing compound Latrunculin-A after mfisi-1 treatment caused complete disruption of actin cables and patches and caused mitochondrial nets to collapse and aggregate, consistent with published observations. These observations indicate that the effect of mfisi-1 on mitochondrial morphology is not the result of secondary changes in either the actin cytoskeleton or ER network and suggests that mfisi-1 produces net-like structures by directly influencing mitochondrial fission.

Structure-activity Analysis of mfisi-1

To determine what structural features are important for the effects of mfisi-1 on mitochondrial fission, we identified structurally related molecules using a chemoinformatics approach. We utilized web-based ChemNavigator to search available public and commercial compound databases for small molecules that uniquely represented key structural features of mfisi-1. We tested a total of 15 small molecules related to mfisi-1 for their effects on mitochondrial morphology in yeast, each at a concentration of 50 μM (Table 3).

TABLE 3

| Small molecules tested | Tested further | % net-like structures |
|---|---|---|
| 3-(2,4-Dichloro-5-methoxy-phenyl)-2-mercapto-3H-quinazolin-4-one | mfisi-1 | 60 |
| 2-Mercapto-3-o-tolyl-3H-quinazolin-4-one | | 30 |

TABLE 3-continued

| Small molecules tested | Tested further | % net-like structures |
|---|---|---|
| 7-chloro-3-(2,4-Dichloro-5-methoxy-phenyl)-2-methylsulfanyl-3H-quinazolin-4-one | mfisi-1.1 | 7 |
| 3-(2,4-Dichloro-5-methoxy-phenyl)-2-methylsulfanyl-3H-quinazolin-4-one | mfisi-1.2 | 7 |
| 3-Benzyl-2-methylsulfanyl-3H-quinazolin-4-one | | 5 |
| (4-oxo-3-phenyl-3,4-dihydro-quinazolin-2-ylsulfanyl)-acetic acid | | 5 |
| 7-chloro-3-(2,4-Dichloro-5-isopropoxy-phenyl)-2-methylsulfanyl-3H-quinazolin-4-one | mfisi-1.3 | 2 |
| 2-Ethylsulfanyl-3-m-tolyl-3H-quinazolin-4-one | | 2 |
| 6-chloro-3-(2,4-Dichloro-5-methoxy-phenyl)-2-methylsulfanyl-3H-quinazolin-4-one | mfisi-1.4 | 2 |
| 2-Allylsulfanyl-3-m-tolyl-3H-quinazolin-4-one | | 1 |
| 2-Methylsulfanyl-3-m-tolyl-3H-quinazolin-4-one | | 0 |
| 2-Mercapto-3-m-tolyl-3H-quinazolin-4-one | | 0 |
| 2-Mercapto-3-(2-methoxy-phenyl)-3H-quinazolin-4-one | | 0 |
| 2-Allylsulfanyl-3-benzyl-3H-quinazolin-4-one | | 0 |
| 2-Allylsulfanyl-(2-methoxy-phenyl)-3H-quinazolin-4-one | | 0 |
| 2,3-Digydor-thiazolo[2,3-b]quinazolin-4-one | | 0 |

In no case did we identify a compound that was more potent/efficacious than mfisi-1; rather most compounds had partial or no activity when examined in our assay for mitochondrial morphology. In fact, our structure-activity analysis identified highly related mfisi-1 structural derivatives that are completely-inactive in vivo. These four derivatives, termed mfisi-1.1-mfisi-1.4, have been useful as tools in other assays of fission-related activities to determine the target and the specificity of mfisi-1 effects (Table 3).

Integration of our results indicates that at least two features are important for the effect of mfisi-1 on mitochondrial morphology in yeast cells (FIG. 9A, in red): an unblocked sulfhydryl moiety that substitutes the quinazolinone and limited rotation about the nitrogen-phenyl bond. Indeed, the substitutions on the phenyl ring of mfisi-1 are predicted to give rise to atropisomers: isomers that are distinct because rotation about a single bond is prevented or greatly slowed. Our data suggest that one of these isomers is selectively active in inhibiting mitochondrial fission. Taken together, our structure-activity analysis indicates that the ability of mfisi-1 to inhibit mitochondrial fission is dependent upon stringent structural requirements, consistent with it being a selective inhibitor.

mfisi-1 is a Selective Inhibitor of the Mitochondrial Dynamin-related GTPase, Dnm1

Figure 10:
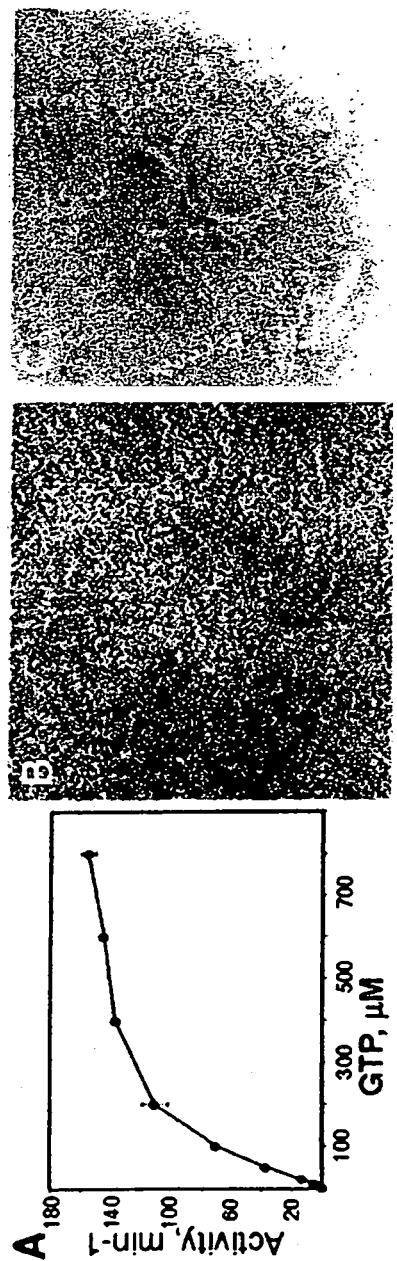
FIG. 10 shows kinetic and structural properties of assembled Dnm1.

In order to discern a detailed mechanism for mitochondrial fission, we have begun to purify and characterize activities associated with known fission components, with the ultimate goal of reconstituting this event in vitro. Towards this goal, we have successfully expressed and purified active recombinant Dnm1 (the yeast mitochondrial fission DRP) from insect cells, using a baculovirus expression system. Using an established radioactive TLC-based assay for GTPase activity, we characterized the kinetic properties of recombinant Dnm1 under low salt conditions (FIG. 10A). Estimations from these assays indicate that the rate of GTP hydrolysis by Dnm1 is ~140 $min^{-1}$, which is comparable to that measured for assembled dynamin (~120 $min^{-1}$). The $K_m$ for GTP for Dnm1 is near 200 μM, greater than that observed for assembled dynamin (~10 μM). The significance of this difference as it relates to the function of these DRPs will be interesting to determine.

Under the low salt conditions used to characterize the GTPase activity, cryo-electron microscopic (EM) analysis showed that Dnm1 self assembles into curved filamentous structures (FIG. 10B), indicating that the described kinetic parameters for Dnm1 are for assembly-stimulated GTPase activity. Furthermore, when incubated with non-hydrolyzable GTP analogs, cryo EM analysis indicated that Dnm1 assembles into spirals of a diameter of 90-100 nm (FIG. 10C). Significantly, the diameter of Dnm1 spirals is greater than the diameter observed for dynamin-1 (40-50 nm), and matches the diameter of mitochondrial membrane constriction sites observed in vivo by immunogold labeling of Dnm1. Given that the diameter of the coated pit neck where dynamin acts during endocytosis is smaller than the diameter of constricted mitochondria where Dnm1 functions, this observation raises the possibility that divergent DRPs have been tailored structurally to associate with different types of intracellular membranes.

Figure 11:
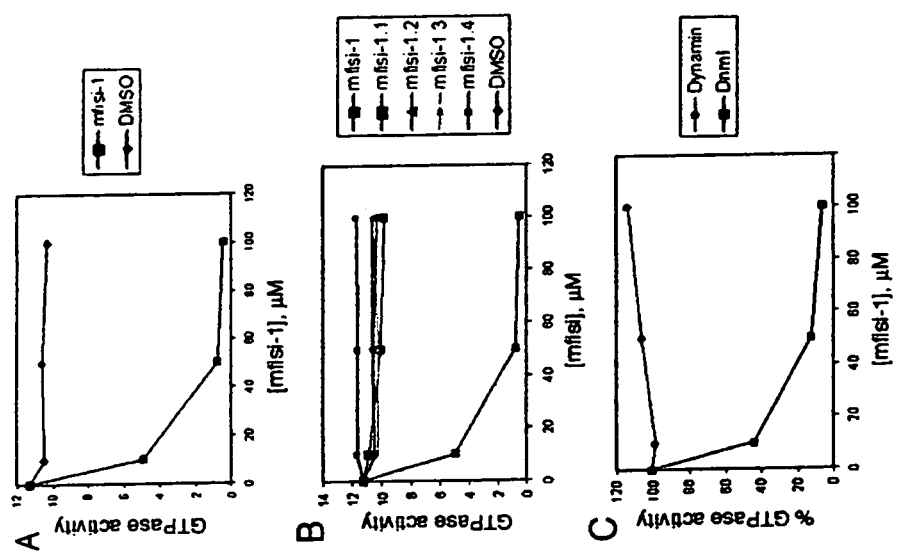
FIG. 11 shows the effects of mfisi-1 and mfisi-1-related compounds on DRP GTPase activity.

We reasoned that the most direct route to identifying an mfisi-1 target was to examine mfisi-1 effects in vitro using pure protein assays. Thus, we tested the effects of mfisi-1 on Dnm1 GTPase activity. As shown in FIG. 11A, mfisi-1 inhibits Dnm1 GTPase activity in a dose dependent manner, with an estimated $IC_{50}$ of ~10 μM. This $IC_{50}$ is nearly identical to the $EC_{50}$ observed for mfisi-1 on the formation of mitochondrial net-like structure in vivo, suggesting that it blocks fission in vivo by inhibiting Dnm1 GTPase activity. In contrast, the two other small molecules identified in our screens for fission inhibitors, mfisi-2 and mfisi-3, had no effect on Dnm1 GTPase activity. Experiments, in which we examined the inhibitory effect of mfisi-1 at its $IC_{50}$ over a broad GTP concentration range (10 μM-2 mM), indicated that mfisi-1 is NOT a pure competitive inhibitor of GTP, making it more likely to be selective and thus a better candidate for a potential therapeutic.

To further test the hypothesis that mfisi-1 blocks mitochondrial fission in vivo by inhibiting Dnm1 GTPase activity, we tested the effects of mfisi-1.1 through mfisi 1.4 for their effects on pure Dnm1 in vitro. The results from two independent double-blinded experiments conclusively demonstrated that these mfisi-1 derivatives do not inhibit Dnm1 GTPase activity (FIG. 11B). The tight correlation between structure and activity further supports the conclusion that a mitochondrial fission target of mfisi-1 in vivo is the mitochondrial fission DRP, Dnm1.

Our observations raise the question of whether mfisi-1 is simply a general inhibitor of GTPase super family members and/or DRPs. It seems unlikely that mfisi-1 is an inhibitor of all GTPase superfamily members, given that it has no effect on GTPase-dependent activities, such as maintenance of the actin cytoskeleton. To more directly address this question, however, we examined the effects of mfisi-1 on the DRP, dynamin-1, which functions during endocytosis in the scission of clathrin coated pits from the plasma membrane. Interestingly, mfisi-1 had no effect on assembly-stimulated rates of GTP hydrolysis for dynamin-1 (FIG. 11C). In contrast, in control reactions performed simultaneously under identical conditions, mfisi-1 was observed to inhibit Dnm1 GTPase activity, indicating that the small molecule was active (FIG. 11C). These results indicate that mfisi-1 is also not a general DRP inhibitor. We will continue to explore the specificity of mfisi-1 for DRPs by determining its effects on the mammalian Dnm1 ortholog, Drp1. We will also examine the yeast mitochondrial fusion DRP, Mgm1, although our time-lapse analysis of mitochondria suggests that mfisi-1 does not significantly affect mitochondrial fusion. Taken together, our data are consistent with mfisi-1 functioning in vivo as a selective inhibitor of the dynamin-related GTPase, Dnm1, to block mitochondrial fission.

Figure 12:
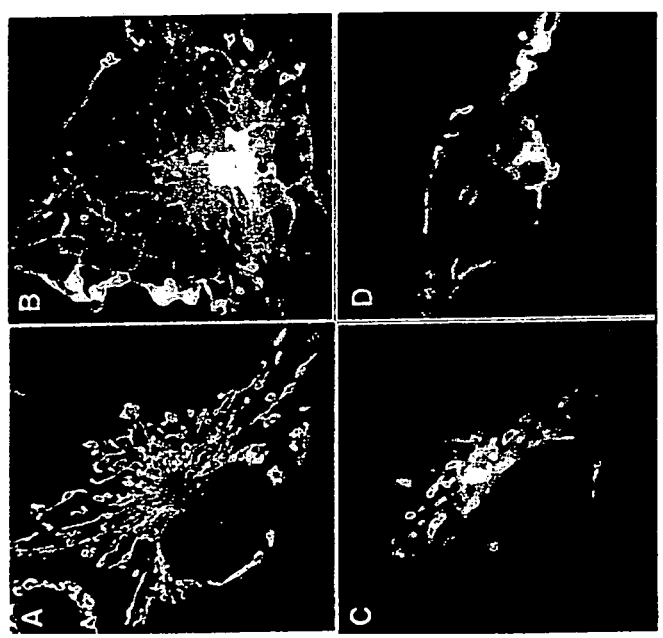
FIG. 12 shows mfisi-1 causes mitochondrial net-like structures to form in mammalian COS cells.
Figure 13:
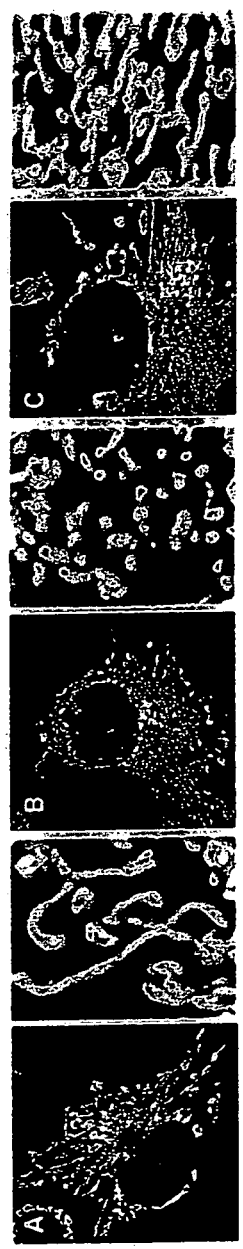
FIG. 13 shows mfisi-1 blocks mitochondrial fragmentation induced by STS.

In a related aspect, as stated above, the structure function analyses indicat that limited rotation about the nitrogen-phenyl bond in mfisi-1 is important for its activity. this observation further suggests that this bond is chiral and synthesis of mfisi-1 will give rise to a racemic mixture of isomers, only one of which is likely to be an active mitochondrial fission inhibitor. To test this hypothesis, isomers can be purified separately using a chiral column and HPLC. Each isomer is then tested for fission activity. For example, the following compounds are envisaged for this use:

mfisi-1 Causes Changes in Mitochondrial Morphology in Mammalian Cells that Phenocopy Mitochondrial Fission Drp1, the mammalian mitochondrial fission DRP, has a high degree of similarity and identity to its yeast ortholog, Dnm1. This encouraged us to exploit the chemical genetic approach and examine the effects of mfisi-1 on mitochondrial morphology in mammalian cells. In mammalian cells, it has been established that when fission is retarded by expression of dominant-negative Drp1, mitochondria become progressively more interconnected, form net-like structures, and collapse into degenerate perinuclear structures in cells. Remarkably, the addition of mfisi-1 to mammalian COS cells in culture caused a rapid and reversible change in mitochondrial morphology equivalent to that observed upon expression of dominant negative Drp1 in double-binded experiments (FIG. 12, n=100: untreated; 0% collapsed nets, 14% loose nets, 70% reticular, 15% fragmented; mfisi-1 treated; n=100, 19% collapsed nets, 45% loose nets, 36% reticular, 0% fragmented). The $EC_{50}$ of mfisi-1 effects on mitochondrial morphology in mammalian cells is similar to that observed for the effect of mfisi-1 on mitochondrial morphology in yeast ($EC_{50}$=10 μM). In addition, structural derivatives of mfisi-1 that do not affect mitochondrial morphology in yeast and do not inhibit Dnm1 GTPase activity, also do not affect mitochondrial morphology in mammalian COS cells. Thus, the characteristics of mfisi-1's effect on mitochondria in mammalian cells are similar to those observed in yeast cells and, by extension, suggest that mfisi-1 inhibits mitochondrial fission in vivo in mammalian cells by inhibiting Drp1 activity. Our findings demonstrate the power of the chemical genetic approach and will enable us to use mfisi-1 to determine the physiological role of mitochondrial fission in apoptosis.

mfisi-1 Blocks Mitochondrial Fission Induced by Apoptotic Signals in Mammalian Cells As indicated above, we observed that mfisi-1 causes changes in mitochondrial morphology in mammalian cells that are consistent with a block in mitochondrial fission. Thus, we examined the effects of mfisi-1 on mitochondrial fragmentation caused by the intrinsic apoptotic stimulus staurosporine (STS) in mammalian COS cells. As shown in FIG. 13, STS-stimulation caused a significant increase in mitochondrial fragmentation in cells. In comparison, in cells treated with STS and 50 μM mfisi-1, mitochondrial fragmentation was significantly reduced (FIG. 12, n=100: untreated; 0% collapsed nets, 14% loose nets, 70% reticular, 15% fragmented; STS treated; n=100, 0% collapsed nets, 0% loose nets, 14% reticular, 86% fragmented; STS and mfisi-1 treated; n=100, 0% collapsed nets, 8% loose nets, 46% reticular, 46% fragmented). In addition we observed that expression of dominant-negative Drp1 also inhibited STS-induced mitochondrial fragmentation, in agreement with published observations. These observations indicate that mfisi-1 retards apoptosis-stimulated Drp1-dependent mitochondrial fission.

Given the demonstrated importance of mitochondrial fission for apoptotic cell death, our data suggest that mfisi-1 also will retard this event in mammalian cells.

Example 5

Research Design and Methods to Carry Out the Experiments

Use mfisi-1 to Probe the Mechanistic Role of Dynamin-related GTPases in Mitochondrial Fission.

1) Determine the Mechanism of misi-1's Inhibition of Dnm1's GTPase Activity in Vitro and of Mitochondrial Fission In Vivo.

Pure protein assays: The assays described below measure two functionally critical DRP activities: GTPase and self-assembly. The GTPase cycle and the self-assembly of Dnm1 are closely interconnected; self-assembly has a direct stimulatory effect on the GTPase activity of dynamin via intermolecular interactions between the GED and GTPase domain. Thus, to help determine the mechanism by which mfisi-1 inhibits Dnm1 GTPase activity, we will examine the effects of mfisi-1 on pure Dnm1 GTPase activity under unassembled and assembled states. Conversely, we will examine the effects of mfisi-1 on Dnm1 assembly under different nucleotide binding states. We will also examine mutant forms of Dnm1 that we have created and are in the process of characterizing using the assays described below. Our collection includes: the Dnm1 GTPase domain, Dnm1 mutants predicted to be retarded at specific points of the GTPase cycle (K41A, S42N, T62D/F, point mutations in the canonical GTP boxes), and Dnm1 mutants which we know are defective for self-assembly in vivo (G385D, V701K, point mutants in the middle domain and GED). To further probe the specificity of mfisi-1, we will examine the effects of mfisi-1 on two additional DRPs which we have expressed and purified from insect cells using the baculovirus expression system: Drp1, the mammalian ortholog of Dnm1, and Mgm1, the yeast mitochondrial fusion DRP. Using the baculovirus expression system, we have been able to purify more than adequate amounts of Dnm1 for these assays. We anticipate the same outcome for the other DRPs we will examine.

Determining the mechanism of mfisi-1 inhibition is critical for assessing how DRPs function in mitochondrial fission. We will perform standard steady-state kinetic assays to determine the mechanism of inhibition by mfisi-1 using established GTPase assays in the presence of variable concentrations of substrate (GTP) and mfisi-1. Our current assay monitors GTP hydrolysis using $\alpha$-$P^{32}$-radiolabeled GTP. Nucleotides are resolved using thin layer chromatography, and quantification of GTP and GDP product is performed using a Phosphorimager. All rates are calculated using time points where product formation is linear over time.

Using this assay, we already know from our previous analysis that mfisi-1 is NOT a pure competitive inhibitor of Dnm1. A Dixon plot of the 1/rate vs. [inhibitor] at variable concentrations of substrate will establish whether the inhibitor acts in a pure noncompetitive or uncompetitive manner or whether it is a mixed type inhibitor.

In the future, we will also use a malachite green-based assay, which sensitively detects inorganic phosphate, to measure the rates of GTP hydrolysis. Although this assay does not allow for the quantification of both substrate and product, it is colorimetric based and, thus, many more reactions can be processed simultaneously.

We have already demonstrated by cryo-EM that in the absence of nucleotides, Dnm1 self-assembles into curved filaments, and in the presence of non-hydrolyzable GTP analogs, extended spiral structures. We will assess how mfisi-1 affects the degree of Dnm1 assembly and the structural dimensions of the assembled structures (diameters of spirals, helical pitch) by cryo-EM. We will also extend these structural studies to examine the effects of mfisi-1 in the presence of GTP, GDP, and non-hydrolyzable GTP analogs on assembled Dnm1. In addition to cryo-EM, a simple centrifugation assay, which is used routinely for the analysis of DRP assembly, will be employed to examine the effects of mfisi-1 on Dnm1 assembly.

In vivo mitochondrial fission assays: We have developed a collection of cytological, biochemical and two-hybrid assays that monitor the stepwise assembly of fission components in yeast. Using these assays, as detailed below, we have characterized events that occur in fission in wild type cells and have determined their functional significance by analyzing mutant forms of fission proteins.

To gain insight into the events that regulate mitochondrial fission, we have characterized cytologically the behavior of mitochondria and fission proteins (Dnm1, Fis1, Mdv1) in both wildtype yeast cells and mutant yeast cells that are blocked for fission. Functional fluorescent versions of the two other fission proteins, dsRed(dimer)-Mdv1 and GFP-Fis1 also have been examined in detail. These cytological assays have allowed us to characterize distinct mechanistic steps in the process of fission that are detailed below, including specific interactions between the Mdv1 N-terminal extension and Fis1, and between the Mdv1 C-terminal WD and Dnm1.

Using our fluorescently tagged fission proteins and time-lapse analysis of live yeast cells, we can determine what step in the fission pathway mfisi-1 affects. For example, if mfisi-1 causes Dnm1 punctate structures to disperse in the cytosol, similar to Dnm1-V701K (see below), we would predict that mfisi-1 affects Dnm1 assembly. Alternatively, mfisi-1 may not affect Dnm1 assembly, but may prevent Mdv1 from interacting with Dnm1 assembled structures on the membrane. This observation would suggest that mfisi-1 stabilizes or mimics the GDP or GTP bound form of Dnm1. The cytological analysis of mfisi-1 will be complementary to the pure protein assays above and the assays for fission protein interactions described below.

In summary, we observe that Dnm1 assembles to form numerous, dynamic puncta that are both associated with mitochondria and that are extra-mitochondrial. From analysis of Δfis1 cells, we observe that Fis1 is required to efficiently target both assembled Dnm1 structures and Mdv1 to the mitochondrial outer membrane. Mdv1 associates exclusively with Dnm1 structures that are localized on the mitochondrial membrane, presumably because Mdv1 is stably tethered via Fis1 to mitochondria. Finally, we observe that only a subset of assembled Dnm1/Mdv1 wild type structures go on to complete a fission reaction in a manner that is dependent on Fis1.

Specific GTPase domain mutations affect Dnm1 behavior in vivo. In cells expressing Dnm1-GTPase domain mutants Dnm1-S42N and -T62F/D, which are predicted to be preferentially in the GDP- and GTP-bound states respectively, fission is blocked and mutant Dnm1 exhibits aberrant assembly and localization, as seen by the presence of just a few, large, bright, Dnm1 punctae. Also, assembled Dnm1-S42N and -T62D/F structures lose their ability to interact with Mdv1 on the mitochondrial membrane. Dnm1-K41A, which is predicted to be unoccupied by nucleotides, is also unable to support fission. Interestingly, however, assembled Dnm1-K41A structures are quantitatively localized to mitochondria and bound to Mdv1. Two-hybrid analysis (see below) of Dnm1-K41A also reveals that this mutant interacts more robustly with Mdv1 than does wild type Dnm1. These observations have led us to believe that one important role of Mdv1 in fission is to create a rate-limiting step by preventing Dnm1 GTP binding and hydrolysis.

The in vivo behavior of Dnm1 also can be affected by mutations in either the middle domain or the GED. In vivo, the middle domain mutant, Dnm1-G385D, is mostly unassembled, as evidenced by a large cytoplasmic pool of Dnm1 and a reduction in the number and sizes of assembled Dnm1 structures. Additionally, assembly of Dnm1-G385D puncta depends upon Fis1, as supported by the disappearance of puncta in the fis1Δ strain. Dnm1-V701K, a GED mutant, also displays an unassembled phenotype in vivo, as seen by the uniform, cytosolic distribution of Dnm1V701K-GFP.

We have successfully demonstrated an interaction between Mdv1 and Fis1 in vivo using chemical crosslinking followed by immunoprecipitation with anti-Mdv1 and anti-Fis1 antibodies. We will use this assay to determine whether mfisi-1 influences the Mdv1-Fis1 interaction. Interactions with Dnm1 have proven difficult to detect biochemically, likely because of the dynamic nature of Dnm1 structures in vivo. However, we have successfully utilized the established two-hybrid assay for protein-protein interactions to demonstrate that Dnm1 interacts with Mdv1 and to confirm that Mdv1 interacts with Fis1. In addition, this assay has proven useful for mapping the Mdv1 domains responsible for interactions with Dnm1 and Fis1. Our most recent use of this assay has been to analyze interactions between site-directed mutants of Dnm1 and Mdv1, where we have obtained data consistent with our cytological findings outlined above.

We have used the plasmids, libraries and yeast host strain for our studies. This system allows interactions between the "bait" (GAL4 binding domain fusion protein) and "prey" (GAL4 activating domain fusion protein) plasmid constructs to be detected using simple plate growth assays (growth on media lacking either histidine or adenine) or enzymatic assays (β-galactosidase activity from lacZ reporter). We propose to create null PDR1 and PDR3 mutations in these two-hybrid yeast strains to test the effect of mfisi-1 and other compounds on the two-hybrid fission protein interactions using liquid P-galactosidase assays. Based on our small molecule screening experience, we know that these mutations enhance the retention of small molecules in yeast cells. This approach has been used successfully in a recent screen for small molecule inhibitors of a Ras/Raf-1 interaction.

2) Probe the Structural Basis of mfisi-1's Inhibition of Fission Using Detailed Structure-activity and Genetic Analyses.

The structure-activity and genetic approaches described utilize mfisi-1 and will by their nature increase our mechanistic understanding of mitochondrial fission beyond that obtained from the experiments in previous examples.

For a subset of small molecules described in this proposal, we will generate second generation compounds. As discussed previously, we have focused on the characterization of the fission inhibitor, mfisi-1. We will produce a library of mfisi-1 derivatives. Second generation mfisi-1 small molecule derivatives will be analyzed for their effects on Dnm1 GTPase activity and mitochondrial morphology in yeast and mammalian cells as described. Results from these experiments will i) further characterize the structurally important features of mfisi-1, ii) provide a stringent test of our hypothesis that the in vivo target of mfisi-1 is the mitochondrial fission DRP, and iii) identify more potent/efficacious mfisi-1 derivatives.

Chemical Synthesis of mfisi-1 derivatives. Here we have outlined several different strategies for the creation of mfisi-1-related compounds. Our functional characterization of these mfisi-1 derivatives will determine what synthetic strategy will be used. While the synthetic route to this mfisi-1, which is 3-(2,4-dichloro-5-methoxyphenyl)-2-mercapto-3H-quinazolin-4-one, is not documented in the literature, we can surmise that it was prepared as outlined to the right (1).

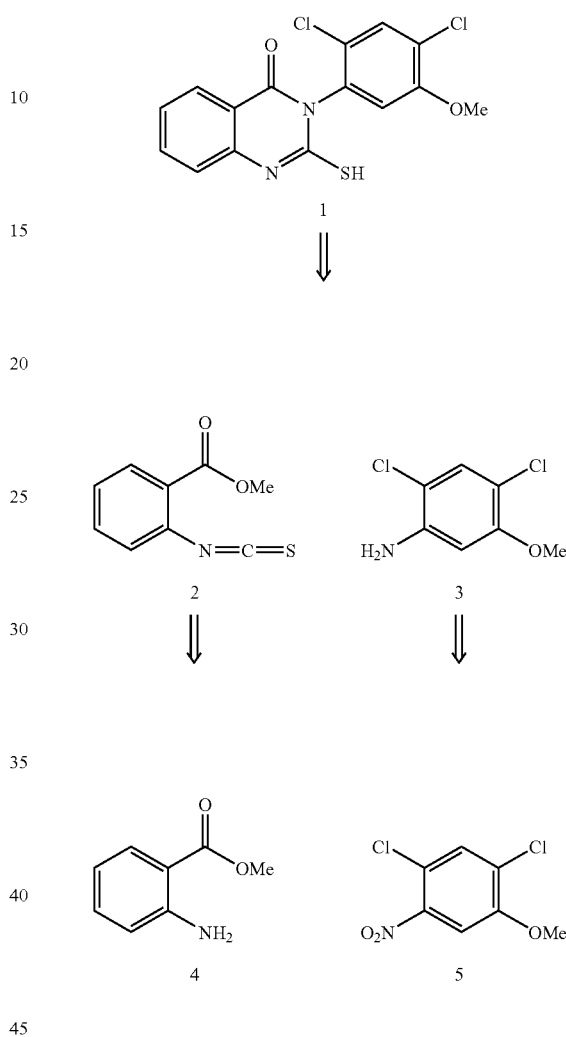

Namely, condensation of amine 3 with the thioisocyanate of 2 followed by cyclotransamination would deliver the 2-sulfanyl-3H-quinazolin-4-one heterocycle. Intermediates 2 and 3 would in turn be readily prepared from commercial aminobenzoate 4 (thiophosgene treatment)[93] and nitrobenzene 5 (—NO$_2$—NH$_2$ reduction).

Building on this chemistry, our plan is to prepare a collection of 2-sulfanyl-3H-quinazolin-4-one combinatorial libraries using solid-phase organic synthesis methodology. As outlined in the figure below, library L.I.1 will be prepared by O-coupling various nitrophenols to Wang resin followed by nitro-amine reduction to give 6. From here, thioisocyanate condensation/cyclotransamination with 7 followed by S-alkylation and subsequent resin cleavage (TFA treatment) will deliver L.I.1. Ten inputs for each diversity element (D1-D3) would deliver 1000 L.I.1 library members. Of course, we will also liberate the non-5-alkylated intermediates to give library L.I.2. Also, if a leading "hit" is identified in library L.I.1, it will be resynthesized on a preparative scale so that O-alkylated analogs of it can be prepared for screening.

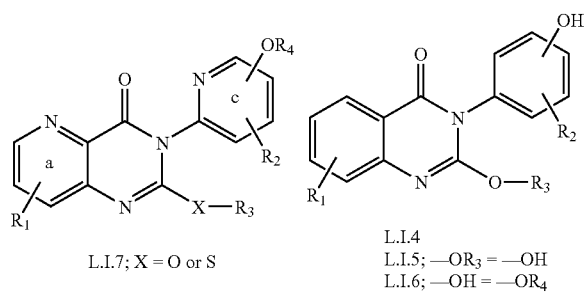
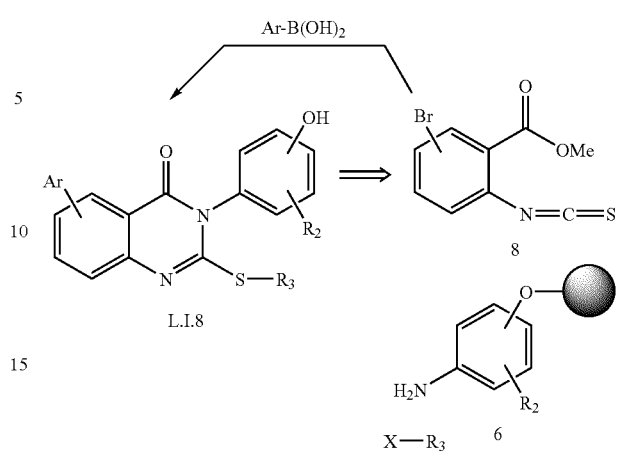

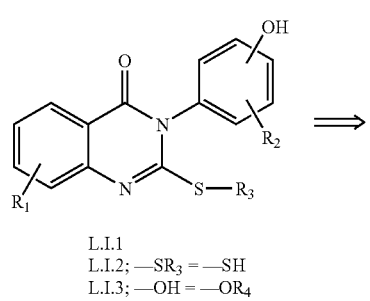

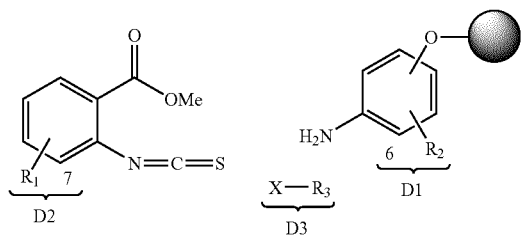

This third library, L.I.3, could easily accommodate 20-30 diversity elements at $R_4$. Libraries L.I.4/.5/.6 represent 2-hydroxy and/or 2-alkoxy analogs of L.I.1/.2/.3, respectively, and will be prepared from the corresponding isocyanate of 7. Finally, all of these libraries can be prepared as nitrogen heterocyclic analogs as represented by library L.I.7 (note: nitrogen can be incorporated in both rings 'a' and 'c', into either ring 'a' or 'c', at various positions in rings 'a'/'c', and twice in rings 'a'/'c').

The synthetic efforts outlined in the preceding scheme will provide a great deal of structure-function information about mfisi-1. That said, the Suzuki coupling strategy outlined below offers even greater substrate modification potential as 150+ boronic acid derivatives are commercially available (see ChemFiles, Vol. 2, No. 1, Aldrich: Products for Suzuki Coupling).

We will perform the Suzuki coupling on resin after the thio-isocyanate condensation/cyclotransamination of 6 and 8. Of course, a number of the modifications discussed for L.I.1-.7 could also incorporate this Suzuki coupling strategy and will be investigated as warranted.

A specific 2-sulfanyl-3H-quinazolin-4-one (9) that hints at the structural diversity available by the chemistries outlined above is depicted below.

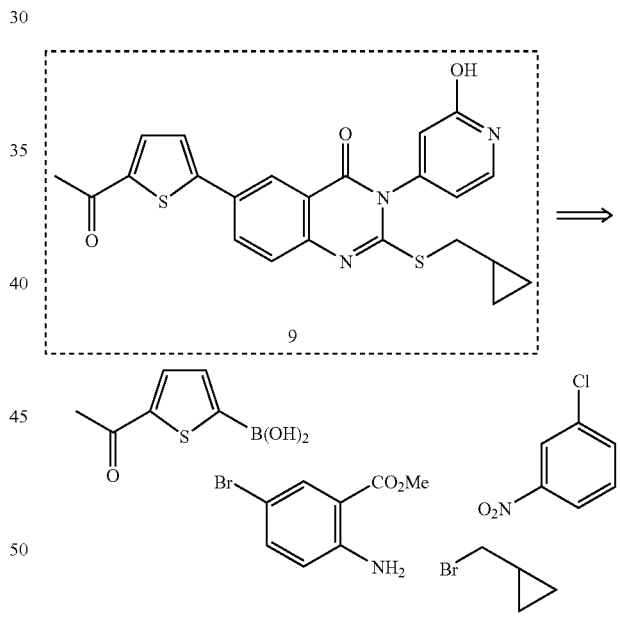

This example points out that the requisite resin-bound aniline intermediate (see 6 above) can be prepared by IPSO substitution of chloride from 2-chloro-4-nitropyridine followed by nitro-amine reduction. Also, all of the building blocks required for this synthesis are commercially available.

All of the routes outlined above for the preparation of libraries L.I.1-.8 can be modified to replace the "—OH" tether with a "—$CO_2H$" tether leading to libraries of generic structure L.I.9. The central change here is that resin-bound aniline intermediate 6 will be replaced with resin-bound aniline intermediate 10.

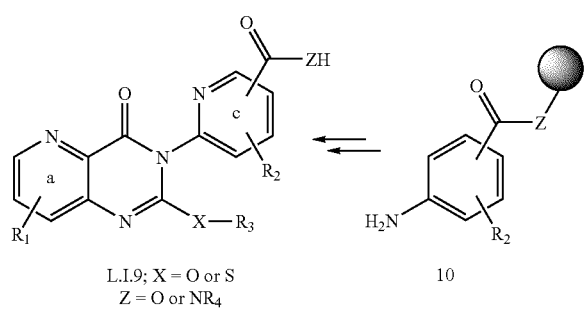

L.I.9; X = O or S
Z = O or NR₄

When Z=O, L.I.9 will be delivered as a carboxylic acid-containing library. Replacing Z=O with Z=NR (Rink-amide type resins) will lead to the production of carboxamide L.I.9 libraries (and introduce another diversity element). Ring 'a' or 'c' Suzuki coupling can also be accomplished with this linker strategy.

We will also explore tethering strategies that couple the nascent 2-sulfanyl-3H-quinazolin-4-one heterocycle via the 'a' ring (the above strategies all are tethered via the 'c' ring). As outlined below, these approaches will lead to libraries of generic structure L.I.10 or L.I.11.

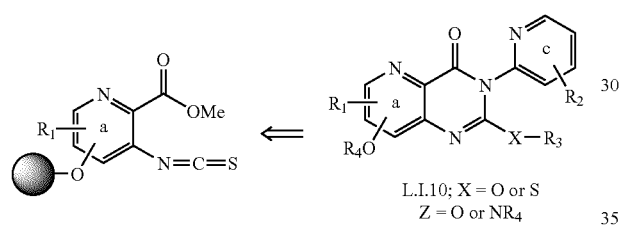

L.I.10; X = O or S
Z = O or NR₄

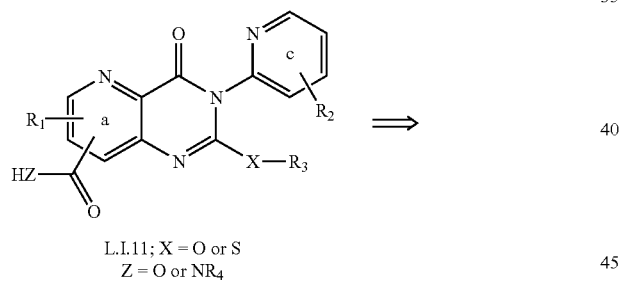

L.I.11; X = O or S
Z = O or NR₄

Finally, below is outlined a novel "traceless" (i.e, no tethering remnant remaining in the product) solid-phase route to the 2-sulfanyl-3H-quinazolin-4-one heterocycle. This strategy is built around the observation that, as reported, N-aryl-2-[[[(ary)amino]carbonyl]amino]benzamides (e.g., 11 where the 'polymer bead'=C₆H₅ and X=O) are (i) stable to isolation but (ii) upon mild heating with base undergo cyclotransamination to the corresponding 2-hyroxy-3H-quinazolin-4-one (e.g., 11→12). By porting this to solid-phase, we can prepare a broad-spectrum library of generalized structure L.I.12, which is devoid of "OH" or "COZH" tethering functionality.

Moreover, resin-bound intermediate 11 can be constructed such that $R_1$ and/or $R_2$ is a bromine which would set the stage for a Suzuki coupling reaction ahead of the cyclotransamination. Of course, S- or O-alkylation to introduce $R_3$ would have to be effected after the substrate is liberated from the resin support.

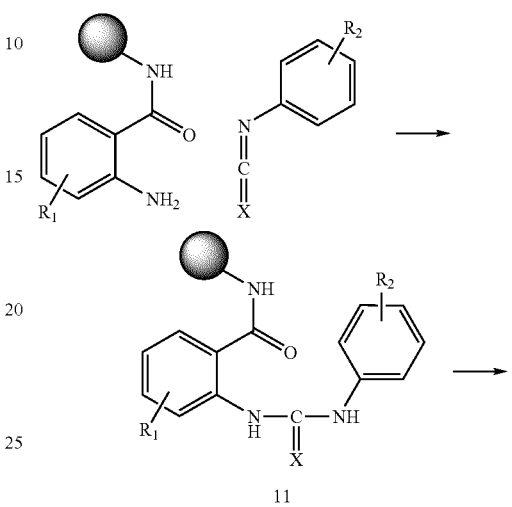

11

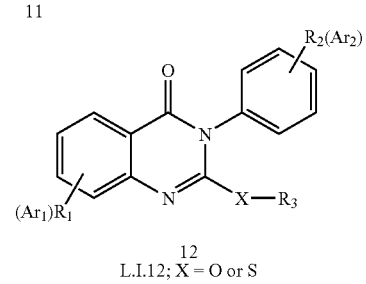

12
L.I.12; X = O or S

The libraries L.I.1-.12 collectively embrace an impressive number of analogs of mfisi-1; from commercial and/or readily available building blocks, we can easily envision >10,000 analogs in this series. Furthermore, many more variants of the chemistry delineated here can be pursued and will be dictated by the results from our mitochondrial fission assays. To illustrate this point, consider analog 13 which we could prepare from tetrahydrobenzo[b]thiophene derivative 14 (easily prepared by the Gewald reaction) and commercially available (Aldrich) quinoline 15 and benzofuranoic acid 16 by modifying the traceless route to library L.I.12 as follows.

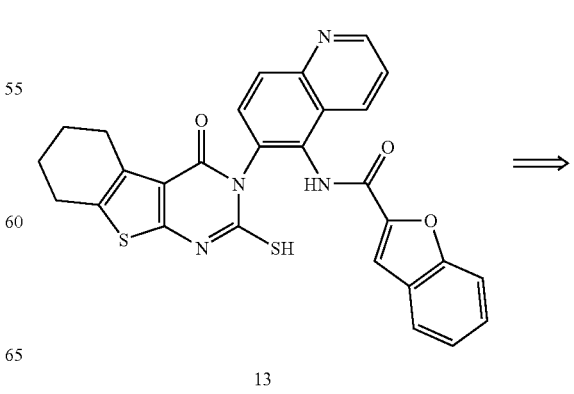

13

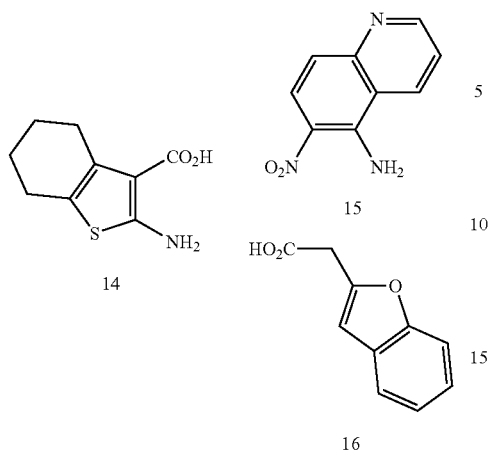
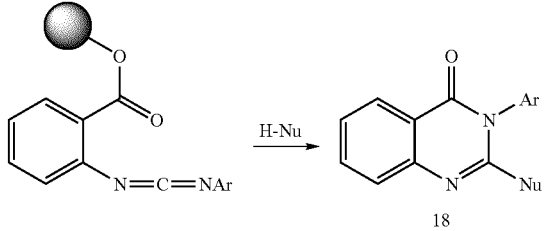

Once urea 11 is constructed with $R_2$=BocNH, the Boc group can be removed and the resulting amine acylated (here with 16). Subsequent cyclotransamination would deliver resin free 13. Employing a modest number (5) of analogs of 14, 15 (10), and 16 (50) would deliver a library of analogs of 13 totaling 2,500 members.

Finally, quinazolines are well known and studied heterocycles, which afford rich and varied biological activity. Due to the long-standing interest in this class of heterocycle, numerous methods have been developed for their preparation. One particularly intriguing method pioneered by Molina and co-workers is outlined below and involves application of the aza-Wittig reaction of iminophosphoranes which are in turn derived from N-substituted o-azidobenzamides.

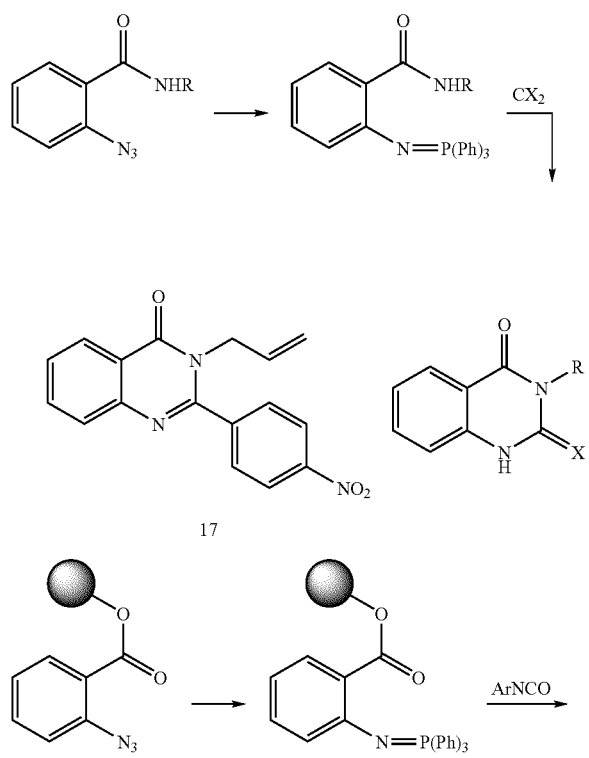

Eguchi and co-workers employed a variant of this chemistry to prepare 3-allyl-2-(4-nitrophenyl)-4(3H)-pyrido-[2,3-d]pyrimidinone (17; see above). An intriguing report by Ding et al. suggests the scheme outlined to the right may have real potential as a "traceless" route to heterocycles like 18. This and other strategies will be dictated by the results we obtain from our mitochondrial fission assays.

Assays for second-generation mfisi-1 derivatives. We anticipate screening approximately 100 mfisi-related compounds initially. Derivatives of mfisi-1 first will be tested at 1, 10 and 100 µM for i) their effects on Dnm1 and Drp1 GTPase activity using the malachite-green based assay in a 96 well format, ii) their effects on mitochondrial morphology in yeast using fluorescent microscopes at UCDavis, and iii) their effects on mitochondrial morphology in mammalian cells using automated microscopes. The systems perform iterative auto-focusing in each well and require 40-90 minutes to image a 384-well plate, making even larger scale screening possible. Results from each assay for a given compound will be compared and will serve to guide our synthetic strategies. Correlation of ability to inhibit Dnm1 GTPase activity in vitro and mitochondrial fission in vivo will lend further support to our hypothesis that the in vivo mitochondrial fission target for mfisi-1 is a DRP. Efficacious mfisi-1 compounds will be further characterized using the assays outlined in the examples of this application.

Genetic Approaches. We will perform a forward screen for mutations in yeast that are resistant and super-sensitive to mfisi-1. In addition, we will perform a focused screen for mutations in the DRP Dnm1 that confer resistance and super-sensitivity using a library of randomly mutagenized DNM1 genes in yeast. This approach has been successful in identifying in vivo targets of other small molecules, such as Brefeldin A, as well as in providing structural insight into the mechanism of inhibition. Mutations that cause resistance and super-sensitivity may not only reside in direct targets of mfisi-1, such as Dnm1, but also in components that interact with targets and thus may reveal new fission proteins. This information, in turn, will provide valuable insight into the mechanism of mitochondrial fission.

We initially identified mfisi-1 and other potential fission inhibitors using a simple growth-based assay for small molecules that suppressed the glycerol growth phenotype of the temperature sensitive fusion mutant, fzo1-1. We will use this same assay to identify mfisi-1 resistant and super-sensitive yeast mutants. Specifically, to identify mfisi-1 resistant mutants, we will screen for mutations that when present in fzo1-1 yeast cells cause mfisi-1 to have no effect on growth at permissive and non-permissive temperatures (lack of suppression). Conversely, to identify super-sensitive mutants we will screen for mutations that when present in fzo1-1 cells, result in slower growth in glycerol at permissive temperature only in the presence of mfisi-1. For these screens, cells will be mutagenized to 90% kill on glycerol with UV light after plating on solid rich glycerol media (YPEG). Mutagenized yeast colonies will be screened for temperature sensitive growth on YPEG by replica plating onto YPEG plates in the absence and presence of mfisi-1. mfisi-1 will be top-plated onto the solid YPEG media under conditions that result in suppression of the temperature sensitive glycerol growth defect of control naïve fzo1-1 cells. Growth will be examined at permissive and non-permissive temperatures and comparisons to control naïve fzo1-1 will be used to determine supersensitive and resistant strains. Mitochondrial morphology in the presence and absence of mfisi-1 will be examined and used as a secondary assay. In addition, we will test these strains with our other structurally diverse small molecules that block fission and fusion to test allele specificity and rule out uninteresting mutations that cause changes in small molecule uptake and elimination from yeast cells. As warranted, mutant strains will be further characterized using the detailed fission assays described above.

Standard genetic techniques will be used to determine whether mutant phenotypes are recessive or dominant and whether phenotypes results from mutations at a single locus, which will be pursued with priority. To identify mutations that confer mfisi-1 resistance and super-sensitivity, we will initially sequence the three fission gene loci (DNM1, FIS1 and MDV1) of our strongest candidate mutants. If no mutations are found, we will use standard genetic techniques to clone the wild type alleles of mfisi-1 resistant and super-sensitive strains.

To identify mfisi-1 resistant Dnm1 mutations, we will use a library of randomly mutagenized DNM1 genes on a yeast expression plasmid, which we have already created using mutagenic PCR and a PCR megapriming strategy (average of 1 mutation/500 bp DNM1). We will screen functional Dnm1 proteins for resistance and super-sensitivity to mfisi-1 by examining strains that contain DNM1 plasmids that restore temperature-sensitive glycerol growth to fzo1-1Δdnm1 cells. These yeast strains subsequently will be screened for resistant and super-sensitive mfisi-1 mutants using the strategies described above.

Characterizing and Defining the Targets of Already Identified Small Molecule Inhibitors.

Figure 9:
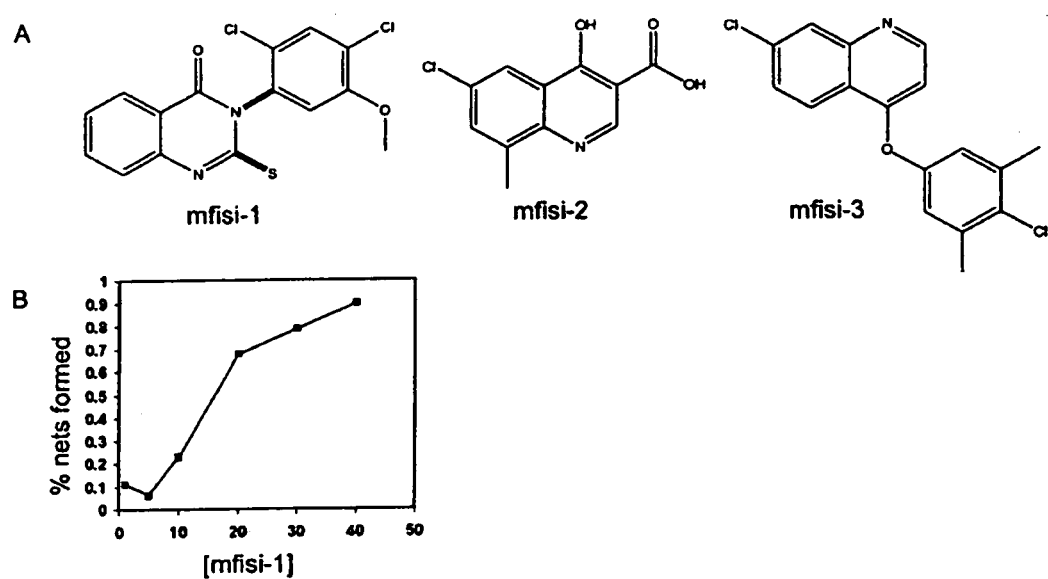
FIG. 9 shows characterization of small molecule fission inhibitors.

Prioritization and characterization of mfisi-2 and mfisi-3: In our screens for mitochondrial fission inhibitors, we identified three compounds. The characterization of one of these, mfisi-1, has been described in detail. The other two small molecules, which we term mfisi-2 and mfisi-3, are structurally in the same class of quinaline derivatives and thus are likely to affect mitochondrial dynamics via the same mechanism (FIG. 9). Given this and the fact that mfisi-2 is significantly more efficacious that mfisi-3, we have focused our characterization efforts on mfisi-2.

Time-lapse analysis of mitochondrial dynamics in the presence of mfisi-2 reveal that it significantly inhibits the rate of mitochondrial fission in cells, but does not stimulate the rate of fusion, as compared to control cells. This observation suggests that mfisi-2, like mfisi-1, causes net-like structures to form in cells by inhibiting fission and not by activating fusion. We will perform structure-activity analysis of mfisi-2, by identifying and characterizing commercially available structurally-related compounds using a similar approach as described for mfisi-1.

To determine the target of mfisi-2, we will characterize this small molecule using the assays for fission. We will also determine whether mfisi-2 affects mitochondrial morphology in mammalian cells. If this is the case, then mfisi-2 might inhibit mitochondrial fission by affecting conserved fission-related activities. As previously stated, mfisi-2 (and mfisi-3) has no effects on Dnm1 GTPase activity, which would suggest that it has effects on other aspects of DRP activity or other conserved components, such as Fis1. If mfisi-2 produces mitochondrial net-like structures in mammalian cells, we will determine its effects on apoptosis as described previously. Prioritization and characterization of potential mitochondrial fusion inhibitors In our screens for mitochondrial fusion inhibitors, we identified a total of 37 compounds. All 37 compounds identified cause mitochondrial tubules to fragment in yeast cells, which is consistent with a block in fusion and ongoing Dnm1-dependent mitochondrial fission. To determine whether fragmentation in drug-treated cells is strictly dependent upon Dnm1-dependent fission, we determined the effects of these small molecules on mitochondrial morphology in Δdnm1 cells. If the compounds specifically block fusion, they should phenocopy, for example, Δfzo1 Δdnm1 cells and should not alter the net-like mitochondrial morphology of Δdnm1 cells. None of the compounds caused complete fragmentation of mitochondria in Δdnm1 cells, as expected based on our growth screen. However, 19 small molecules did cause partial mitochondrial fragmentation phenotypes, suggesting that they cause mitochondrial fragmentation in wild type cells via mechanisms not strictly dependent upon fission and fusion components and thus will not be characterized further.

To prioritize the remaining 15 small molecules, we have grouped them by structure into classes. We have determined that the compounds fall into six classes. Five of these contain multiple related members and the sixth class is a collection of single member molecules as shown below.

Structural classes of small molecule fusion inhibitors

Class I 1-phenoxy-1,3-dinitrobenzene

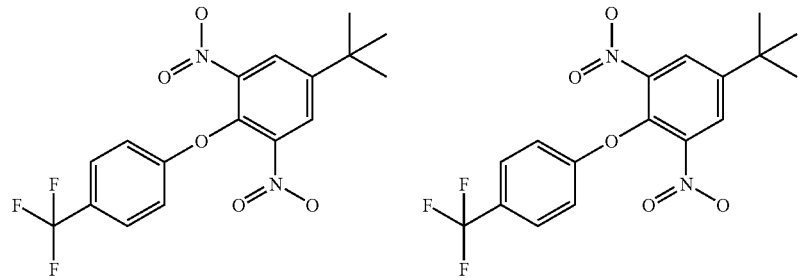

Class II 1H-pyrazole

-continued
Structural classes of small molecule fusion inhibitors
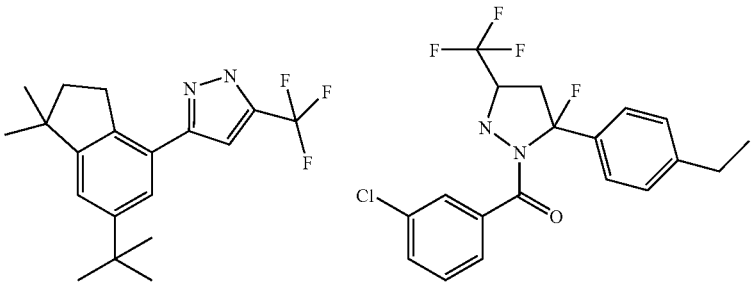 [SMILES: CC(C)(C)c1cc(-c2cc(C(F)(F)F)[nH]n2)c2c(c1)C(C)(C)CC2 ; CCc1ccc(C2(F)CC(C(F)(F)F)NN2C(=O)c2cccc(Cl)c2)cc1]
Class III [1,2,5]oxadiazolo[3,4-b]pyrazine
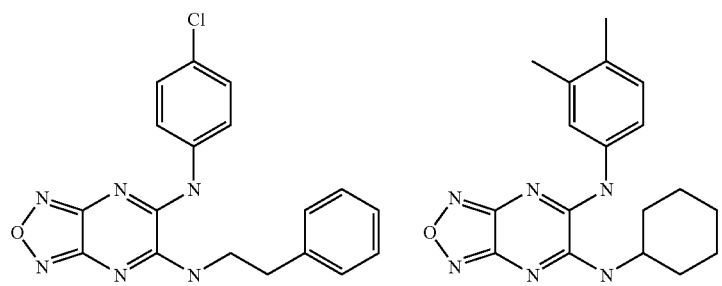
Class IV sulfonamide
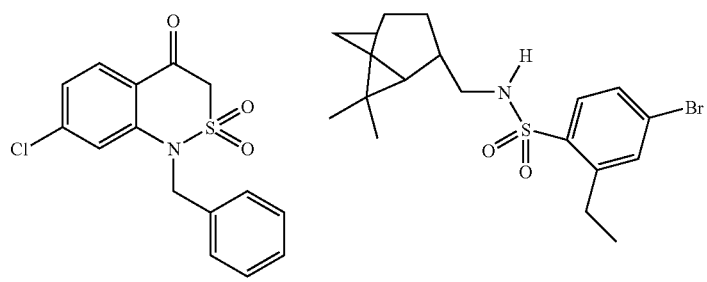 [SMILES: O=C1CS(=O)(=O)N(Cc2ccccc2)c2cc(Cl)ccc21 ; CCc1cc(Br)ccc1S(=O)(=O)NCC1CCC2CC23C1C3(C)C]
Class V thiazolidin-4-one
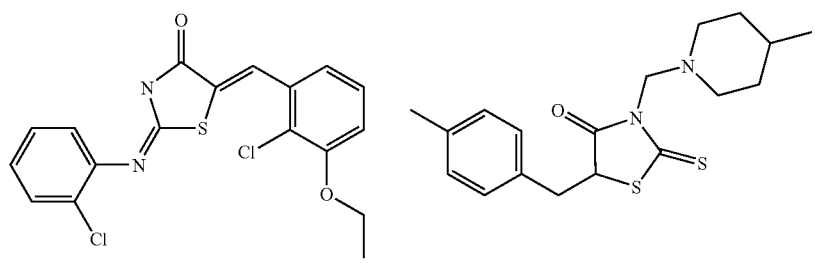
Single Member Classes
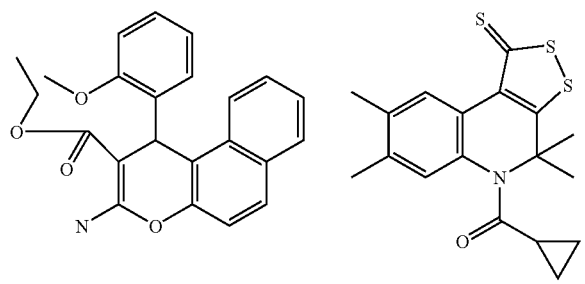

| Structural classes of small molecule fusion inhibitors |
|---|

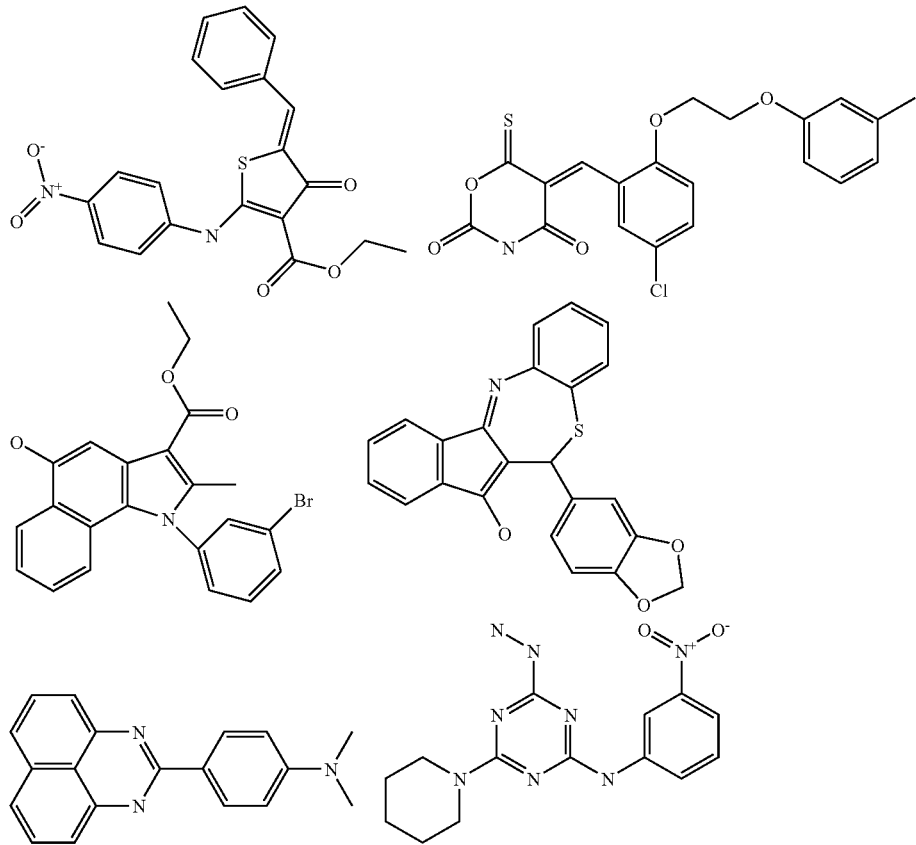

To further prioritize these six classes, we will determine the potency/efficacy of each of the 15 small molecules by examining their ability to cause mitochondrial fragmentation in yeast cells over 1-100 µM concentration range. We will determine whether they cause mitochondrial fragmentation by activating fission or by retarding fusion by examining their effects in vivo using time-lapse analysis of mitochondrial dynamics. If we discover small molecules that activate fission, we will analyze them using the assays outlined previously. For fusion inhibitors, we will choose the three most potent/efficacious, structurally unique small molecules and pursue them with the highest priority using the assays described below. To identify which structural features of these compounds are important for their activity, we will identify and characterize commercially available structurally-related compounds using a similar approach as described for mfisi-1 and will compare compounds within the same structural class identified in our screens. Also, as part of our preliminary characterization, we will examine the effects of these small molecules on mitochondrial morphology in mammalian cells. Assays for target identification and mechanistic characterization of small molecule fusion inhibitors. The assays described below have been developed in the yeast model system. Our long-term goal is to develop similar assays for mammalian mitochondrial fusion.

Figure 14:
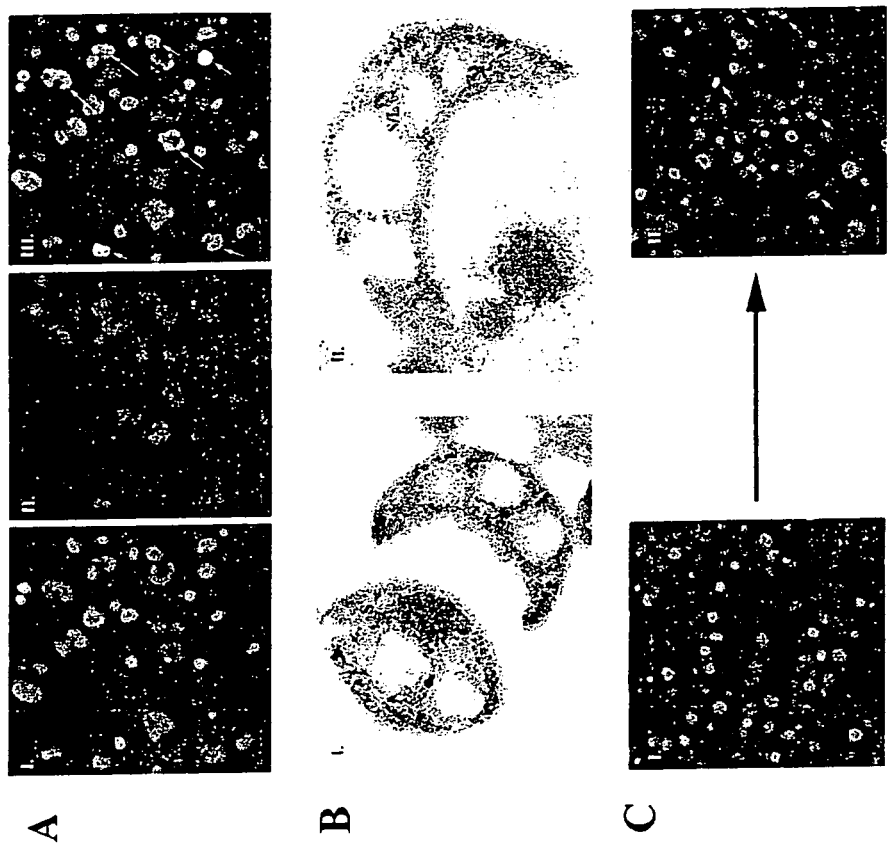
FIG. 14 shows mitochondrial fusion in vitro.

In vitro fusion assay: We have developed a cytological assay for in vitro mitochondrial fusion based upon simple mitochondrial matrix content mixing (FIG. 14). Specifically, crude mitochondria containing either matrix-targeted-GFP or matrix-targeted-dsRED are prepared from yeast, mixed together in equal amounts and concentrated by centrifugation. Concentrated mitochondria are resuspended in a fusion-promoting reaction mix containing energy and cytosol, and aliquots are removed and analyzed by fluorescence microscopy using a Deltavision Deconvolution microscope. Several observations indicate that mitochondrial fusion occurs under our assay conditions. First, we observe the co-localization of matrix-targeted green and red fluorophores in a sub-population of mitochondria. Mitochondria that are labeled with GFP and dsRed are larger than single-labeled structures (FIG. 14A, Panel I-III arrows), and the fluorescent signal of these mitochondria are decreased in intensity, as fluorophores are diluted within an increased vesicle size (FIG. 14A, Panel III arrows). Based on this content-mixing assay, we estimate that 15% of mitochondria in vitro fuse after 30 minutes. Using this assay, we have determined that mitochondrial fusion requires: GTP hydrolysis, cytosol, and the presence of the fusion proteins, Fzo1, Mgm1 and Ugo1, in trans. To validate our light microscopy evidence for fusion and to clearly visualize both membranes for the analysis of intermediates, immuno-electron microscopy was performed using antibodies generated to both GFP and dsRED on mitochondria prepared from reactions conducted in the presence and absence of energy, where fusion is promoted or blocked, respectively, as assessed by light microscopy. Electron micrographs confirmed the co-localization of matrix-dsRed and -GFP in mitochondria only under conditions that promote mitochondrial fusion, confirming the results of our light microscopy-based assay (marked by different sized gold particles) (FIG. 14B, Panel II).

Analyses of in vitro fusion reactions using fluorescence microscopy and EM analysis have revealed intermediates in the fusion process (FIG. 14C). In the presence of non-hydrolyzable GTP, unfused but tightly docked mitochondrial structures, with deformed membranes at the regions of contact, accumulate (FIG. 14C, Panel II). Analysis of the efficiency of fusion versus time, indicates that these docked structures correlate with dilution-resistant fusion activity, confirming that they are tightly coupled. We are currently placing interactions among fusion components in the context of this assay, using co-immunoprecipitation techniques (see below) and an analysis of the effects of mutated forms of the fusion proteins, Fzo 1, Mgm1, and Ugo1.

To help determine their mechanism of action and to more stringently test for their specificity as mitochondrial fusion inhibitors, we will determine the effects of our small molecules in this in vitro assay for mitochondrial fusion. In the event that a small molecule does not affect mitochondrial fusion in vitro, we will not pursue it further. It is our hope that small molecules will identify novel intermediates in this assay or phenocopy the results we obtain with a particular mutant fusion component. We will use the results from this analysis to guide further experiments aimed at identifying the targets of fusion inhibitors, which may involve the development of additional assays and longer-term characterization, such as second-generation small molecule library construction. As a test for specificity, mfisi-1 will also be examined in this assay.

Biochemical assays We have successfully demonstrated Mgm1/Fzo1, Mgm1/Ugo1 and Fzo1/Ugo1 interactions in vivo using chemical crosslinking followed by immunoprecipitation with antibodies directed against these fusion proteins or associated tags. In addition, we have developed an assay for Pcp1-dependent Mgm1 processing, which is an important event for fusion. Specifically, yeast cells are pulse labeled with $S^{35}$-Methionine and the conversion of Mgm1 precursor to product is quantified by autoradiography of anti-Mgm1 immunoprecipitates. We will determine the effects, if any, of small molecules in these assays.

Future pure protein assays under development We are in the process of developing pure protein assays for fusion proteins. Specifically, our goal is to develop GTP hydrolysis assays for both Mgm1 and for the cytosolic GTPase domain of the transmembrane Fzo1. To obtain sufficient quantities of these proteins, we are currently in the process of expressing and characterizing several variations of each of these proteins in insect cells, using the baculovirus expression system. This approach has proven successful for Dnm1. We will test our small molecule fusion inhibitors in these pure protein assays. As a test for specificity, mfisi-1 will also be examined in Fzo1 and Mgm1 GTPase assays.

Longer-term characterizations Results from the detailed characterization of fusion inhibitors will guide the decision of creating second-generation libraries of these molecules. Also as a longer-term goal, we will isolate and characterize mutants that are resistant to our potential fusion inhibitors to gain greater insight into their mechanism of action, using approaches that are conceptually similar to those outlined for mfisi-1.

Examine the Physiological Role of Mitochondrial Membrane Dynamics in Regulating Apoptosis and Using mfisi-1, mfisi-1 Derivatives, and Other Already Identified Small Molecule Inhibitors of Fission and Fusion.

Assays for stepwise events in apoptosis The effects of small molecules on early to late markers for apoptosis will be examined. All of the assays proposed are well-established and straightforward. As a control for the inhibition of mitochondrial fission-dependent apoptosis, we will determine the effects of expression of dominant negative Drp1s in these assays. The early events of mitochondrial fragmentation and loss of mitochondrial inner membrane potential will be examined under all conditions using the vital membrane potential sensitive dye, Mitotracker (Molecular Probes) according to established methodology. We have already been able to demonstrate with this technique that expression of dominant-negative forms of Drp1 block apoptosis-stimulated mitochondrial fission. The later event of cytochrome c release form the mitochondria intermembrane space will be assessed using both biochemical fractionation/Western blotting and immunofluorescence analyses with commercially available anti-cytochrome c antibodies. A relatively late event in apoptotic cell death is the externalization of plasma membrane phosphatidylserine (PS). This event can be detected using commercially available fluorescently labeled (FITC)-annexin V, which is a Ca2+-dependent phospholipid binding protein with a high affinity for PS, in conjunction with established fluorescent-activated cell sorter (FACS) methodology. The results from these assays will be combined to determine whether small molecules retard or stimulate apoptosis in mammalian cells.

Figure 15:
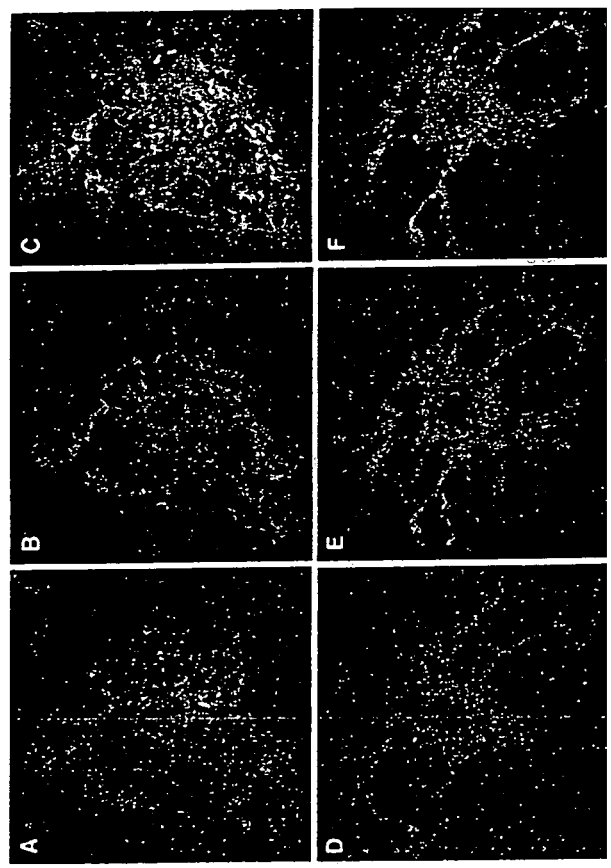
FIG. 15 shows that Drp 1 is mobilized in mammalian COS cells stimulated to undergo apoptosis.
Figure 16:
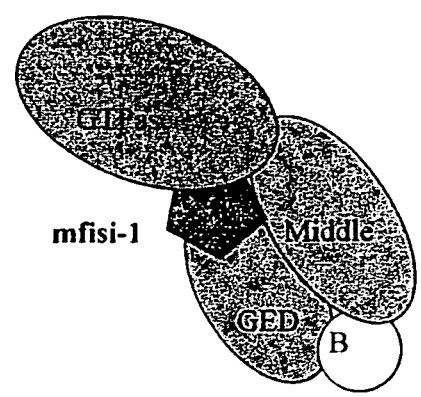
FIG. 16 is an illustration of a model for mfisi-1 action where mfisi-1 binds at the interface between the GTPase, middle and GED domains of Dnm1 to cause inhibitory action.

Cytological assays for mechanistic studies Upon the induction of intrinsic apoptosis, the mitochondrial fission DRP localizes from the cytosol to form foci on the mitochondria, associated with fission sites. The recent finding that the pro-apoptotic Bcl-2 family member, Bax, colocalizes to these Drp1 foci and also to human fusion Mfn2 protein foci in mammalian COS-1 and HeLa cells, suggests that mitochondrial fission and fusion proteins directly regulate the critical event of mitochondrial membrane permeabilization during apoptosis. To test this hypothesis and help determine the mechanism of action of small molecules we identify that affect apoptosis, we will examine the behavior and co-localization of Drp1, Mnf2, and Bax, using fluorescently tagged versions of these proteins and mitochondria, simultaneously, in the presence and absence of our compounds. Using Drp1-GFP, we have observed that STS treatment of COS cell dramatically stimulates the mobilization of assembled Drp1 structures to mitochondria, as previously described (FIG. 15). Results from this proposed cytological analysis of the fission Drp, fusion Mnf2 and pro-apoptotic Bax will provide insight into the mechanism of action of small molecules on apoptosis, and will provide mechanistic insight into the processes of apoptosis and mitochondrial membrane dynamics.

Although the invention has been described with reference to the presently preferred embodiment, it should be understood that various modifications can be made without departing from the spirit of the invention. Accordingly, the invention is limited only by the following claims.

What is claimed is:

1. A method of inhibiting mitochondrial fission in mammalian cells comprising contacting the cells with a compound of the general formula:

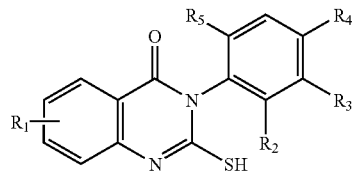

wherein $R_1$ is independently H; a C1-C18 alkyl or C1-C18 heteroalkyl, which may be branched, may be substituted, or combinations thereof; a C1-C18 alkenyl or C1-C18 heteroalkenyl, which may be branched, may be substituted, or combinations thereof; a C1-C18 alkynyl or C1-C18 heteroalkynyl, which may be branched, may be substituted, or combinations thereof; a C3-C18 aryl or C3-C18 heteroaryl, which may contain a bridge, may be substituted, or combinations thereof; or a C5-C18 cycloalkyl or C5-C18 heterocycle, which may contain a bridge, may be substituted, or combinations thereof;

$R_2$ is H; a C1-C18 alkyl or C1-C18 heteroalkyl, which may be branched, may be substituted, or combinations thereof; or a halogen;

$R_3$ is H; a C1-C18 alkyl or C1-C18 heteroalkyl, which may be branched, or may be substituted, or combinations thereof;

$R_4$ is a halogen; and $R_5$ is a halogen, thereby inhibiting mitochondrial fission in the mammalian cells.

2. The method of claim 1, wherein $R_3$ is a C1 heteroalkyl.

3. The method of claim 1, wherein $R_3$ is a C3 heteroalkyl.

4. The method of claim 2, wherein $R_2$ is H.

5. The method of claim 3, wherein $R_2$ is H.

6. The method of claim 3, wherein $R_1$ is independently selected from H or a C1-C18 alkyl.

7. The method of claim 4, wherein $R_1$ is H.

8. The method of claim 4, wherein $R_1$ is a C1 alkyl.

9. The method of claim 5, wherein $R_1$ is H.

10. The method of claim 4, wherein the compound is defined by the structure:

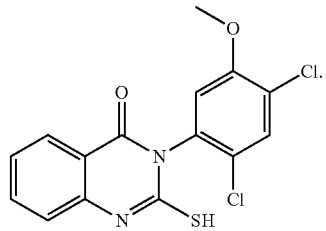 [SMILES: COc1cc(-n2c(S)nc3ccccc3c2=O)c(Cl)cc1Cl]

11. A method of inhibiting mitochondrial fission in mammalian cells comprising contacting the cells with a compound defined as 2-mercapto-3-(2-(trifluoromethyl)phenyl)quinazolin-4(3H)one, thereby inhibiting mitochondrial fission in the mammalian cells.

12. A method of inhibiting apoptosis in cells comprising contacting the cells with a compound of the general formula:

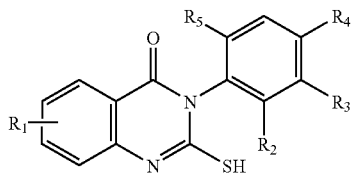

wherein $R_1$ is independently H; a C1-C18 alkyl or C1-C18 heteroalkyl, which may be branched, may be substituted, or combinations thereof; a C1-C18 alkenyl or C1-C18 heteroalkenyl, which may be branched, may be substituted, or combinations thereof; a C1-C18 alkynyl or C1-C18 heteroalkynyl, which may be branched, may be substituted, or combinations thereof; a C3-C18 aryl or C3-C18 heteroaryl, which may contain a bridge, may be substituted, or combinations thereof; or a C5-C18 cycloalkyl or C5-C18 heterocycle, which may contain a bridge, may be substituted, or combinations thereof;

$R_2$ is H; a C1-C18 alkyl or C1-C18 heteroalkyl, which may be branched, may be substituted, or combinations thereof; or a halogen;

$R_3$ is H; a C1-C18 alkyl or C1-C18 heteroalkyl, which may be branched, or may be substituted, or combinations thereof;

$R_4$ is a halogen; and $R_5$ is a halogen, thereby inhibiting apoptosis in the cells.

* * * * *

UNITED STATES PATENT AND TRADEMARK OFFICE
CERTIFICATE OF CORRECTION

PATENT NO. : 8,450,333 B2 Page 1 of 1
APPLICATION NO. : 12/028536
DATED : May 28, 2013
INVENTOR(S) : Jodi Nunnari et al.

It is certified that error appears in the above-identified patent and that said Letters Patent is hereby corrected as shown below:

IN THE SPECIFICATION

In Col. 1, beginning at line 13, please amend the paragraph below as follows:

~~This invention was made in part with government support under Grant No. NIH/GM 62942 awarded by the National Institutes of Health (NIH). The government may have certain rights in this invention.~~

This invention was made with Government support under Grant No. GM 062942, awarded by the National Institutes of Health. The Government has certain rights in the invention.

Signed and Sealed this
Tenth Day of September, 2013

Teresa Stanek Rea
*Acting Director of the United States Patent and Trademark Office*